(12) United States Patent
Zheng et al.

(10) Patent No.: US 10,371,892 B2
(45) Date of Patent: Aug. 6, 2019

(54) NANOSTRUCTURED PHOTONIC MATERIALS

(71) Applicant: BOARD OF REGENTS, THE UNIVERSITY OF TEXAS SYSTEM, Austin, TX (US)

(72) Inventors: Yuebing Zheng, Austin, TX (US); Linhan Lin, Austin, TX (US); Mingsong Wang, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/935,383

(22) Filed: Mar. 26, 2018

(65) Prior Publication Data

US 2018/0275343 A1 Sep. 27, 2018

Related U.S. Application Data

(60) Provisional application No. 62/476,992, filed on Mar. 27, 2017.

(51) Int. Cl.
*G02B 5/00* (2006.01)
*G02B 6/12* (2006.01)
(Continued)

(52) U.S. Cl.
CPC ........... *G02B 6/1226* (2013.01); *G02B 5/008* (2013.01); *G02B 6/1225* (2013.01);
(Continued)

(58) Field of Classification Search
None
See application file for complete search history.

(56) References Cited

U.S. PATENT DOCUMENTS 9,059,388 B2 * 6/2015 Tahan .................... H01L 49/006
9,647,182 B2 * 5/2017 Verschuuren ......... H01L 33/504
(Continued)

OTHER PUBLICATIONS

Alam, Muhammad Z. et al., "A marriage of convenience: Hybridization of surface plasmon and dielectric waveguide modes", Laser Photonics Rev. 2014, 8, 394-408.
(Continued)

*Primary Examiner* — Jerry Rahll
(74) *Attorney, Agent, or Firm* — Meuiner Carlin & Curfman LLC

(57) ABSTRACT

Disclosed herein are nanostructured photonic materials, methods of making and methods of use thereof, and systems including the nanostructured photonic materials. The nanostructured photonic materials comprise a substrate having a first surface; an array comprising a plurality of spaced-apart plasmonic particles disposed on the first surface of the substrate; and a waveguide layer disposed on the array and the first surface, wherein the waveguide layer: is optically coupled to the array, comprises a photochrome dispersed within a matrix material, and has an average thickness defining a hybrid plasmon waveguide mode; wherein the photochrome exhibits a first optical state and a second optical state; and wherein the second optical state of the photochrome at least partially overlaps with the hybrid plasmon waveguide mode.

16 Claims, 30 Drawing Sheets

(51) Int. Cl.
G02B 6/122 (2006.01)
G02B 6/13 (2006.01)
G01N 21/552 (2014.01)

(52) U.S. Cl.
CPC ....... G01N 21/554 (2013.01); G01N 2201/08 (2013.01); G02B 6/13 (2013.01); G02B 2006/1215 (2013.01); G02B 2006/12071 (2013.01)

(56) References Cited

U.S. PATENT DOCUMENTS

| | | | |
|---|---|---|---|
| 9,709,504 B2* | 7/2017 | Osterlund | G01N 21/552 |
| 9,995,460 B2* | 6/2018 | Verschuuren | H01L 33/502 |
| 10,088,114 B2* | 10/2018 | Lunz | F21K 9/64 |
| 2011/0217544 A1* | 9/2011 | Young | B29C 37/0032 |
| | | | 428/327 |

OTHER PUBLICATIONS

Arango, Felipe B. et al., "Plasmonic Antennas Hybridized with Dielectric Waveguides", ACS Nano 2012, 6, 10156-10167.
Baudrion, Al et al., "Reversible Strong Coupling in Silver Nanoparticle Arrays Using Photochromic Molecules", Nano Lett. 2013, 13, 282-286.
Bukasov, R. et al., "Probing the Plasmonic Near-Field of Gold Nanocrescent Antennas", ACS Nano 2010, 4, 6639-6650.
Chan, G H. et al., "Localized Surface Plasmon Resonance Spectroscopy of Triangular Aluminum Nanoparticles", J. Phys. Chem. C 2008, 112, 13958-13963.
Chikkaraddy, R et al., "Single-molecule strong coupling at room temperature in plasmonic nanocavities", Nature 2016, 535, 127-130.
Christ, A et al., "Waveguide-Plasmon Polaritons: Strong Coupling of Photonic and Electronic Resonances in a Metallic Photonic Crystal Slab", Phys. Rev. Lett. 2003, 91, 183901.
Christopoulos, S et al., "Room-Temperature Polariton Lasing in Semiconductor Microcavities." Phys. Rev. Lett. 2007, 98, 126405.
Daskalakis, et al., "Nonlinear interactions in an organic polariton condensate", Nat Mater 2014, 13, 271-278.
Dintinger, J et al., "Molecule-Surface Plasmon Interactions in Hole Arrays: Enhanced Absorption, Refractive Index Changes, and All-Optical Switching", Adv. Mater. 2006, 18, 1267-1270.
Eizner, E et al., "Aluminum Nanoantenna Complexes for Strong Coupling between Excitons and Localized Surface Plasmons", Nano Lett. 2015, 15, 6215-6221.
Englund, D et al., "Controlling the Spontaneous Emission Rate of Single Quantum Dots in a Teo-Dimensional Photonic Crystal", Phys. Rev. Lett. 2005, 95, 013904.
Fan, et al., "DNA-Enabled Self-Assembly of Plasmonic Nanoclusters," Nano Lett. 2011, 11, 4859-4864.
Fevrier, M et al., "Giant Coupling Effect between Metal Nanoparticle Chain and Optical Waveguide", Nano Lett. 2012, 12, 1032-1037.
Fofang, et al., "Plexcitonic Nanoparticles: Plasmon-Exciton Coupling in Nanoshell-J-Aggregate Complexes", Nano Lett. 2008, 8, 3481-3487.
Gunter, et al., "Sub-cycle switch-on of ultrastrong light-matter interaction", Nature 2009, 458, 178-181.
Halas, et al., "Plasmons in Strongly Coupled Metallic Nanostructures", Chem. Rev., 2011, 111 (6), pp. 3913-3961.
Hennessy, et al., "Quantum nature of a strongly coupled single quantum dot-cavity system" Nature 2007, 445, 896-899.
Hutchinson, et al., "Modifying Chemical Landscapes by Coupling to Vacuum Fields", Angew. Chem. Int. Ed. 2012, 51, 1592-1596.
Hutchinson, et al., "Tuning the Work-Function via Strong Coupling", Adv. Mater. 2013, 25, 2481-2485.
Khitrova, et al., "Vacuum Rabi splitting in semiconductors", Nat Phys 2006, 2, 81-90.

Klajn, et al., "Spiropyran-based dynamic materials", Chem. Soc. Rev. 2014, 43, 148-184.
Klar, et al., "Surface-Plasmon Resonances in Single Metallic Nanoparticles", Phys. Rev. Lett. 1998, 80, 4249-4252.
Knight, et al., "Aluminum for Plasmonics", ACS Nano 2014, 8, 834-840.
Konrad, et al., "Strong and Coherent Coupling of a Plasmonic Nanoparticle to a Subwavelength Fabry-Pérot Resonator", Nano Lett. 2015, 15, 4423-4428.
Langhammer, "Localized Surface Plasmon Resonances in Aluminum Nanodisks", Nano Lett. 2008, 8, 1461-1471.
Lidzey, et al., "Room Temperature Polariton Emission from Strongly Coupled Organic Semiconductor Microcavities", Phys. Rev. Lett. 1999, 82, 3316-3319.
Lin, et al., "Optimizing plasmonic nanoantennas via coordinated multiple coupling", Sci. Rep. 2015, 5, 14788.
Lin, et al., "Photoswitchable Rabi Splitting in Hybrid Plasmon-Waveguide Modes", Nano Letters, 2016, 16(12), 7655-7663.
Ming, et al., "Resonance-Coupling-Based Plasmonic Switches", Small, 2010, 6, 2514-2519.
Ni, et al., "Observing Plasmonic-Molecular Resonance Coupling on Single Gold Nanorods", Nano Lett. 2010, 10, 77-84.
Noda, et al., "Spontaneous-emission control by photonic crystals and nanocavities", Nat Photon 2007, 1, 449-458.
O'Brien, et al., "Uniform Circular Disks Wth Synthetically Tailorable Diameters: Two-Dimensional Nanoparticles for Plasmonics", Nano Lett. 2015, 15, 1012-1017.
Olson, et al., "High Chromaticity Aluminum Plasmonic Pixels for Active Liquid Crystal Displays", ACS Nano 2016, 10, 1108-1117.
Oulton, et al., "A hybrid plasmonic waveguide for subwavelength confinement and long-range propagation", Nat Photon 2008, 2, 496-500.
Pirruccio, et al., "Coherent Control of the Optical Absorption in a Plasmonic Lattice Coupled to a Luminescent Layer", Phys. Rev. Lett. 2016, 116, 103002.
Plumhof, et al., "Room-temperature Bose-Einstein condensation of cavity exciton-polaritons in a polymer", Nat Mater 2014, 13, 247-252.
Press, et al., "Photon antibunching from a single quantum-dot-microcavity system in the strong coupling regime", Phys. Rev. Lett. 2007, 98, 117402.
Rodriguez, et al., "Light-Emitting Waveguide-Plasmon Polaritons", Phys. Rev. Lett. 2012, 109, 166803.
Ross, et al., "Aluminum and Indium Plasmonic Nanoantennas in the Ultraviolet", J. Phys. Chem. C 2014, 118, 12506-12514.
Russell, et al., "Gap-mode plasmonic nanocavity", Appl. Phys. Lett. 2010, 97, 163115.
Russell, et al., "Measuring the mode volume of plasmonic nanocavities using coupled optical emitters", Phys. Rev. B 2012, 85, 245445.
Savasta, et al., "Nanopolaritons: Vacuum Rabi Splitting with a Single Quantum Dot in the Center of a Dimer Nanoantenna", ACS Nano 2010, 4, 6369-6376.
Schlather, et al., "Near-Field Mediated Plexcitonic Coupling and Giant Rabi Splitting in Individual Metallic Dimers", Nano Lett. 2013, 13, 3281-3286.
Schwartz, "Reversible Switching of Ultrastrong Light-Molecule Coupling", Phys. Rev. Lett. 2011, 106, 196405.
Shi, et al., "Spatial Coherence Properties of Organic Molecules Coupled to Plasmonic Surface Lattice Resonances in the Weak and Strong Coupling Regimes", Phys. Rev. Lett. 2014, 112, 153002.
Sonnichsen, et al., "Drastic Reduction of Plasmon Damping in Gold Nanorods", Phys. Rev. Lett. 2002, 88, 077402.
Sugawara, et al., "Strong Coupling between Localized Plasmons and Organic Excitons in Metal Nanovoids", Phys. Rev. Lett. 2006, 97, 266808.
Takazawa, et al., "Fraction of a Millimeter Propagation of Exciton Polaritons in Photoexcited Nanofibers of Organic Dye", Phys. Rev. Lett. 2010, 105, 067401.
Tassone, et al., "Exciton-exciton scattering dynamics in a semiconductor microcavity and stimulated scattering into polaritons", Phys. Rev. B 1999, 59, 10830-10842.
Todisco, et al., "Exciton-Plasmon Coupling Enhancement via Metal Oxidation", ACS Nano 2015, 9, 9691-9699.

(56) References Cited

OTHER PUBLICATIONS

Törmä, et al., "Strong coupling between surface plasmon polaritons and emitters: a review", Rep. Prog. Phys. 2015, 78, 013901.

Trügler, et al., "Strong coupling between a metallic nanoparticle and a single molecule", Phys. Rev. B 2008, 77, 115403.

Väkeväinen, et al., "Plasmonic surface lattice resonances at the strong coupling regime", Nano Lett. 2013, 14, 1721-1727.

Van Vugt, "Exciton Polaritons Confined in a ZnO Nanowire Cavity", Phys. Rev. Lett. 2006, 97, 147401.

Vasa, et al., "Ultrafast Manipulation of Strong Coupling in Metal-Molecular Aggregate Hybrid Nanostructures", ACS Nano 2010, 4, 7559-7565.

Vecchi, et al., "Shaping the Fluorescent Emission by Lattice Resonances in Plasmonic Crystals of Nanoantennas", Phys. Rev. Lett. 2009, 102, 146807.

Volz, et al., "Ultrafast all-optical switching by single photons", Nat Photon 2012, 6, 605-609.

Wang, et al., "Molecular-Fluorescence Enhancement via Blue-Shifted Plasmon-Induced Resonance Energy Transfer", J. Phys. Chem. C 2016, 120, 14820-14827.

Weisbuch, et al., "Observation of the coupled exciton-photon mode splitting in a semiconductor quantum microcavity", Phys. Rev. Lett. 1992, 69, 3314-3317.

Wurtz, "Molecular Plasmonics with Tunable Exciton-Plasmon Coupling Strength in J-Aggregate Hybridized Au Nanorod Assemblies", Nano Lett. 2007, 7, 1297-1303.

Yang, et al., "Optical Forces in Hybrid Plasmonic Waveguides", Nano Lett. 2011, 11, 321-328.

Yannopapas, et al., "Electromagnetically induced transparency and slow light in an array of metallic nanoparticles", Phys. Rev. B 2009, 80, 035104.

Yao, et al., "Functional Nanostructured Plasmonic Materials", Adv. Mater. 2010, 22, 1102-1110.

Zengin, et al., "Approaching the strong coupling limit in single plasmonic nanorods interacting with J-aggregates", Sci. Rep. 2013, 3, 3074.

Zengin, et al., "Evaluating Conditions for Strong Coupling between Nanoparticle Plasmons and Organic Dyes Using Scattering and Absorption Spectroscopy", J. Phys. Chem. C 2016, 120, 20588-20596.

Zengin, et al., "Realizing Strong Light-Matter Interactions between Single-Nanoparticle Plasmons and Molecular Excitons at Ambient Conditions", Phys. Rev. Lett. 2015, 114, 157401.

Zentgraf, et al., "Ultranarrow coupling-induced transparency bands in hybrid plasmonic systems", Phys. Rev. B 2009, 80, 195415.

Zheng, et al., "Incident-Angle-Modulated Molecular Plasmonic Switches: A Case of Weak Exciton-Plasmon Coupling", Nano Lett. 2011, 11, 2061-2065.

Zheng, et al., "Color-selective and CMOS-compatible photodetection based on aluminum plasmonics", Adv. Mater. 2014, 26, 6318-6323.

Zhou, et al., "Silver Nanoshell Plasmonically Controlled Emission of Semiconductor Quantum Dots in the Strong Coupling Regime", ACS Nano 2016, 10, 4154-4163.

* cited by examiner

NANOSTRUCTURED PHOTONIC MATERIALS

CROSS-REFERENCE TO RELATED APPLICATIONS

This application claims the benefit of priority to U.S. Provisional Application 62/476,992, filed Mar. 27, 2017, which is hereby incorporated herein by reference in its entirety.

BACKGROUND

The enhanced interaction between light and photon emitters occurs when the emitters are placed in an optical cavity, where the local density of electromagnetic modes is dramatically increased. In the weak-coupling region, where the emitter-cavity energy exchange rate is lower than the cavity decay rate, enhanced light extraction is obtained from the emitter. More significant effects emerge in the strong-coupling region when the emitter-cavity coupling strength is higher than their individual decay rates, e.g., 2 g>γ or κ (Törmä P and Barnes W L. *Rep. Prog. Phys.* 2015, 78, 013901), where g is the coupling energy, γ is the emitter scattering rate and κ is the cavity loss rate. In this region, the emitter and cavity coherently exchange energy and lead to the Rabi oscillations, manifesting as a resonant peak splitting in the optical spectra.

High-quality cavities with small effective cavity volume V ($g \propto 1/\sqrt{V}$) and high quality factor Q ($Q \propto 1/\sqrt{\kappa}$) are expected to support these strongly coupled mixed states for such applications as low-threshold emission (Christopoulos S et al. *Phys. Rev. Lett.* 2007, 98, 126405; Noda S et al. *Nat Photon* 2007, 1, 449-458) and ultrafast switching (Volz T et al. *Nat Photon* 2012, 6, 605-609; Vasa P et al. *ACS Nano* 2010, 4, 7559-7565; Gunter G et al. *Nature* 2009, 458, 178-181). The strong coupling has been demonstrated in a variety of optical cavities, including optical microcavities, optical waveguides, and plasmonic cavities. Most of the dielectric-based microcavities suffer from a large cavity volume and active-area footprint. Metal nanoparticles, which support localized surface plasmon resonances (LSPRs) with tremendous electric field enhancement in the deep subwavelength volumes, provide improved mode confinement and coupling strength. Rabi splitting arises from strong plasmon-molecule coupling. Specifically, Rabi splitting in hybrids of plasmonic nanostructures and molecules has attracted intense interests for both fundamental research and applications in sensing, information processing, and nanolasers. Strong plasmon-molecule couplings have been studied in systems comprising molecule aggregates (or single molecules) and plasmonic nanoparticle arrays (or single-particle cavity). Plasmonic switches have been demonstrated based on hybrids of plasmonic nanoparticles and photochromic molecules. However, plasmonic cavities experience intrinsic loss due to resistive heating in metals, which limits the coupling strength between the plasmons and molecular excitons, and impedes the use of plasmonic cavities in long-range optical guiding and switching. To enable long-distance guiding of surface plasmons with strong subwavelength confinement, researchers have been exploring new modes that arise from the hybridization between surface plasmons and dielectric waveguides, which has been achieved in hybrid plasmonic waveguides.

However, the integration of Rabi splitting into the hybrid plasmon-waveguide modes (HPWMs), which have advantages of both subwavelength light confinement of surface plasmons and long-range propagation of guided modes in dielectric waveguides, as remained elusive. The compositions, methods, and systems discussed herein addresses these and other needs.

SUMMARY

In accordance with the purposes of the disclosed compositions, methods, and systems as embodied and broadly described herein, the disclosed subject matter relates to nanostructured photonic materials, methods of making and methods of use thereof, and systems including the nanostructured photonic materials. In some examples, the nanostructured photonic materials demonstrate photoswitchable Rabi splitting and can be used as optically rewritable photonic waveguides.

Additional advantages of the disclosed systems and methods will be set forth in part in the description which follows, and in part will be obvious from the description. The advantages of the disclosed systems and methods will be realized and attained by means of the elements and combinations particularly pointed out in the appended claims. It is to be understood that both the foregoing general description and the following detailed description are exemplary and explanatory only and are not restrictive of the disclosed systems and methods, as claimed.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

The accompanying figures, which are incorporated in and constitute a part of this specification, illustrate several aspects of the disclosure, and together with the description, serve to explain the principles of the disclosure.

DETAILED DESCRIPTION

Figure 1:
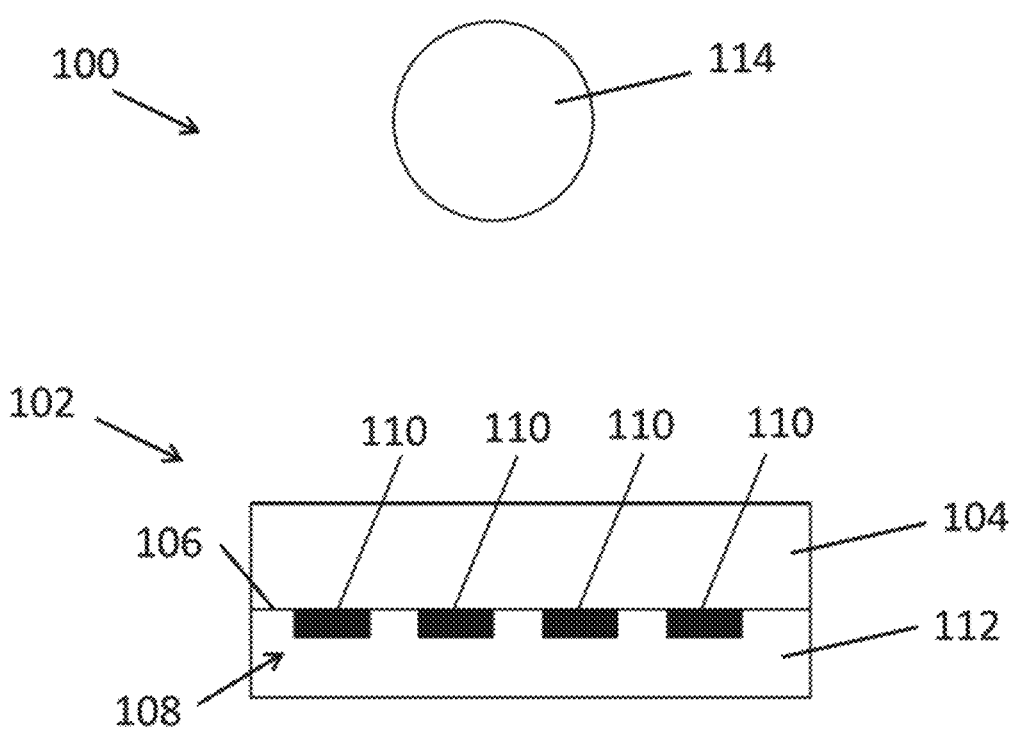
FIG. 1 is a schematic of an exemplary system as disclosed herein.

The compositions, methods, and systems described herein may be understood more readily by reference to the following detailed description of specific aspects of the disclosed subject matter and the Examples included therein.

Before the present compositions, methods, and systems are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Disclosed herein are nanostructured photonic materials, methods of making and methods of use thereof, and systems including the nanostructured photonic materials. In some examples, the nanostructured photonic materials demonstrate photoswitchable Rabi splitting and can be used as optically rewritable photonic waveguides.

Nanostructured Photonic Materials

Disclosed herein are nanostructured photonic materials. As used herein, "nanostructured" means any structure with one or more nanosized features. A nanosized feature can be any feature with at least one dimension less than 1 µm in size. For example, a nanosized feature can comprise a nanowire, nanotube, nanoparticle, nanopore, and the like, or combinations thereof. As such, the nanostructured conducting film can comprise, for example, a nanowire, nanotube, nanoparticle, nanopore, or a combination thereof. In some examples, the nanostructured conducting film can comprise a material that is not nanosized but has been modified with a nanowire, nanotube, nanoparticle, nanopore, or a combination thereof.

The nanostructured photonic materials comprise a substrate having a first surface. The substrate can be any material consistent with the compositions, methods, and systems disclosed herein. In some examples, the substrate can be transparent. As used herein, a "transparent substrate" is meant to include any substrate that is transparent at the wavelength or wavelength region of interest. Examples of substrates include, but are not limited to, glass, quartz, parylene, silicon dioxide, mica, poly(methyl methacrylate), polyamide, polycarbonate, polyester, polypropylene, polytetrafluoroethylene, hafnium oxide, hafnium silicate, tantalum pentoxide, zirconium dioxide, zirconium silicate, and combinations thereof. In some examples, the substrate comprises glass, quartz, silicon dioxide, silicon nitride, a polymer, or a combination thereof.

In some examples, the substrate can be substantially optically transparent. For example, the substrate can have an average transmittance of 75% or more at one or more wavelengths from 350 nm to 800 nm (e.g., 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more). In some examples, the substrate can have an average transmittance of 100% or less at one or more wavelengths from 350 nm to 800 nm (e.g., 99% or less, 98% or less, 97% or less, 96% or less, 95% or less, 94% or less, 93% or less, 92% or less, 91% or less, 90% or less, 89% or less, 88% or less, 87% or less, 86% or less, 85% or less, 84% or less, 83% or less, 82% or less, 81% or less, 80% or less, 79% or less, 78% or less, 77% or less, or 76% or less). The average transmittance of the substrate at one or more wavelengths from 350 nm to 800 nm can range from any of the minimum values described above to any of the maximum valued described above. For example, the substrate can have an average transmittance of from 75% to 100% at one or more wavelengths from 350 nm to 800 nm (e.g., from 75% to 87%, from 87% to 100%, from 75% to 80%, from 80% to 85%, from 85% to 90%, from 90% to 95%, from 95% to 100%, or from 80% to 95%).

In some examples, the substrate can be non-transparent. In the case of a non-transparent substrate, the optical properties of the nanostructured photonic material can, for example, be measured using reflection spectra.

The nanostructured photonic material further comprises an array comprising a plurality of spaced-apart plasmonic particles disposed on the first surface of the substrate. The plurality of plasmonic particles can, for example, each be spaced apart from their nearest neighbors in the array by a distance effective to define an array plasmon energy.

In some examples, the plurality of plasmonic particles can comprise a plasmonic material. Examples of plasmonic materials include, but are not limited to, plasmonic metals (e.g., Au, Ag, Pt, Pd, Cu, Cr, Al, or a combination thereof), plasmonic semiconductors (e.g., silicon carbide), doped semiconductors (e.g., aluminum-doped zinc oxide), transparent conducting oxides, perovskites, metal nitrides, silicides, germanides, and two-dimensional plasmonic materials (e.g., graphene), and combinations thereof.

In some examples, the plurality of plasmonic particles can comprise a plurality of metal particles. The plurality of metal particles can, for example, comprise a metal selected from the group consisting of Au, Ag, Pt, Pd, Cu, Cr, Al, and combinations thereof. In some examples, the plurality of plasmonic particles can comprise a plurality of aluminum particles.

Each of the plurality of plasmonic particles can have an average characteristic dimension. The term "characteristic dimension," as used herein, refers to the largest straight line distance spanning a plasmonic particle in the plane of the first surface. For example, in the case of a plasmonic particle having a substantially circular shape in the plane of the first surface, the characteristic dimension of the plasmonic particle is the diameter of the particle. "Average characteristic dimension" and "mean characteristic dimension" are used interchangeably herein, and generally refer to the statistical mean characteristic dimension of the particles in a population of particles. The characteristic dimension can be measured using methods known in the art, such as evaluation by scanning electron microscopy, transmission electron microscopy, and/or atomic force microscopy.

In some examples, each of the plurality of plasmonic particles can have an average characteristic dimension of 20 nm or more (e.g., 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 550 nm or more, 600 nm or more, 650 nm or more, 700 nm or more, 750 nm or more, 800 nm or more, 850 nm or more, 900 nm or more, or 950 nm or more). In some examples, each of the plurality of plasmonic particles can have an average characteristic dimension of 1000 nm or less (e.g., 950 nm or less, 900 nm or less, 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, or 25 nm or less). The average characteristic dimension of each of the plurality of plasmonic particles can range from any of the minimum values described above to any of the maximum values described above. For example, each of the plurality of plasmonic particles can have an average characteristic dimension of from 20 nm to 1000 nm (e.g., from 20 nm to 500 nm, from 500 nm to 1000 nm, from 20 nm to 200 nm, from 200 nm to 400 nm, from 400 nm to 600 nm, from 600 nm to 800 nm, from 800 nm to 1000 nm, from 30 nm to 300 nm, from 50 nm to 250 nm, or from 100 nm to 200 nm).

In some examples, the plurality of plasmonic particles can be substantially monodisperse. "Monodisperse" and "homogeneous size distribution," as used herein, and generally describe a population of particles where all of the particles have the same or nearly the same characteristic dimension. As used herein, a monodisperse distribution refers to particle distributions in which 80% of the distribution (e.g., 85% of the distribution, 90% of the distribution, or 95% of the distribution) lies within 25% of the mean characteristic dimension (e.g., within 20% of the mean characteristic dimension, within 15% of the mean characteristic dimension, within 10% of the mean characteristic dimension, or within 5% of the mean characteristic dimension).

In some examples, each of the plurality of plasmonic particles can have an average thickness. As used herein, the thickness of a plasmonic particle refers to the largest straight line distance spanning a plasmonic particle in a plane perpendicular to the first surface. For example, in the case of a plasmonic particle having a substantially cylindrical shape, with the cross-section of the plasmonic particle having a circular shape in the plane of the first surface, the thickness of the plasmonic particle is the height of the cylindrical plasmonic particle. "Average thickness" of a plurality of plasmonic particles and "mean thickness" of a plurality of plasmonic particles are used interchangeably herein, and generally refer to the statistical mean thickness of the particles in a population of particles. The thickness of the plurality of plasmonic particles can be measured using methods known in the art, such as evaluation by scanning electron microscopy, transmission electron microscopy, and/or atomic force microscopy.

In some examples, each of the plurality of plasmonic particles can have an average thickness of 10 nm or more (e.g., 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 110 nm or more, 120 nm or more, 130 nm or more, 140 nm or more, 150 nm or more, 160 nm or more, 170 nm or more, 180 nm or more, or 190 nm or more). In some examples, each of the plurality of plasmonic particles can have an average thickness of 200 nm or less (e.g., 190 nm or less, 180 nm or less, 170 nm or less, 160 nm or less, 150 nm or less, 140 nm or less, 130 nm or less, 120 nm or less, 110 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, or 15 nm or less). The average thickness of each of the plurality of plasmonic particles can range from any of the minimum values described above to any of the maximum values described above. For examples, each of the plurality of plasmonic particles can have an average thickness of from 10 nm to 200 nm (e.g., from 10 nm to 100 nm, from 100 nm to 200 nm from 10 nm to 50 nm, from 50 nm to 90 nm, from 90 nm to 130 nm, from 130 nm to 170 nm, from 170 nm to 200 nm, from 20 nm to 50 nm, or from 10 nm to 150 nm).

The plurality of plasmonic particles can comprise particles of any shape (e.g., a sphere, a rod, an ellipsoid, a triangular prism, a pyramid, a polygon, a cylinder, a rectangular prism, etc.). In some examples, the plurality of plasmonic particles can have an isotropic shape. In some examples, the plurality of plasmonic particles can have an anisotropic shape. In some examples, each of the plurality of plasmonic particles is disk-like in shape, such that the diameter of each disk is the average characteristic dimension of each of the plasmonic particles. As used herein, a "disk-like" shaped particle comprises a cylindrically shaped particle wherein the diameter of the cylinder is greater than the height of the cylinder.

The array comprising the plurality of spaced-apart plasmonic particles disposed on the first surface of the substrate can, for example, be defined by a unit cell. As used herein, a "unit cell" is the smallest group of plasmonic particles in the array that constitutes the repeating pattern of the array. The unit cell can have a first principle axis and a second principle axis with an included angle between the first principle axis and the second principle axis. The array is built up of repetitive translations of the unit cell along its principle axes.

The first principle axis has a length that is the distance separating each plasmonic particle in the array from its neighboring plasmonic particle (edge to edge) along the first principle axis. The length of the first principle axis can, for example, be two times the characteristic dimension of the plasmonic particles or less. The length of the first principle axis can be selected, for example, to enhance the electromagnetic coupling between adjacent plasmonic particles along the first principle axis.

In some examples, the length of the first principle axis can be from 5 nm or more (e.g., 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 550 nm or more, 600 nm or more, 650 nm or more, 700 nm or more, 750 nm or more, 800 nm or more, 850 nm or more, 900 nm or more, or 950 nm or more). In some examples, the length of the first principle axis can be 1000 nm or less (e.g., 950 nm or less, 900 nm or less, 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, or 10 nm or less). The length of the first principle axis can range from any of the minimum values described above to any of the maximum values described above. For example, the length of the first principle axis can be from 5 nm to 1000 nm (e.g., from 5 nm to 500 nm, from 500 nm to 1000 nm, from 5 nm to 200 nm, from 200 nm to 400 nm, from 400 nm to 600 nm, from 600 nm to 800 nm, from 800 nm to 1000 nm, from 5 nm to 100 nm, or from 10 nm to 250 nm).

The second principle axis has a length that is the distance separating each plasmonic particle in the array from its neighboring plasmonic particle (edge to edge) along the second principle axis. In some examples, the length of the second principle axis can be $m\lambda/n \sin(\theta)-d$, where $\lambda$ is the wavelength of the hybrid plasmon waveguide mode, n is the refractive index of the waveguide layer, m means mth order of the hybrid plasmon waveguide mode, $\theta$ is the angle between the light propagation direction and the normal direction of the waveguide layer, and d is the average characteristic dimension of the plurality of plasmonic particles.

In some examples, the length of the second principle axis can be 50 nm or more (e.g., 100 nm or more, 150 nm or more, 200 nm or more, 250 nm or more, 300 nm or more, 350 nm or more, 400 nm or more, 450 nm or more, 500 nm or more, 600 nm or more, 700 nm or more, 800 nm or more, 900 nm or more, 1000 nm or more, 1100 nm or more, 1200 nm or more, 1300 nm or more, 1400 nm or more, 1500 nm or more, 1600 nm or more, 1700 nm or more, 1800 nm or more, or 1900). In some examples, the length of the second principle axis can be 2000 nm or less (e.g., 1900 nm or less, 1800 nm or less, 1700 nm or less, 1600 nm or less, 1500 nm or less, 1400 nm or less, 1300 nm or less, 1200 nm or less, 1100 nm or less, 1000 nm or less, 900 nm or less, 800 nm or less, 700 nm or less, 600 nm or less, 500 nm or less, 450 nm or less, 400 nm or less, 350 nm or less, 300 nm or less, 250 nm or less, 200 nm or less, 150 nm or less, or 100 nm or less). The length of the second principle axis can range from any of the minimum values described above to any of the maximum values described above. For example, the length of the second principle axis can be from 50 nm to 2000 nm (e.g., from 50 nm to 1000 nm, from 1000 nm to 2000 nm, from 50 nm to 400 nm, from 400 nm to 800 nm, from 800 nm to 1200 nm, from 1200 nm to 1600 nm, from 1600 nm to 2000 nm, from 100 nm to 300 nm, or from 200 nm to 2000 nm).

The unit cell can be of any shape. In some examples, the unit cell is in the shape of a triangle. In some examples, the unit cell is in the shape of a quadrilateral (e.g., a rectangle, a parallelogram, or the like). In some examples, The included angle between the first principle axis and the second principle axis of the unit cell can, for example, be 45° or more (e.g., 50° or more, 55° or more, 60° or more, 65° or more, 70° or more, 75° or more, 80° or more, 85° or more, 90° or more, 95° or more, 100° or more, 105° or more, 110° or more, 115° or more, 120° or more, 125° or more, or 130° or more). In some examples, the included angle between the first principle axis and the second principle axis of the unit cell can be 135° or less (e.g., 130° or less, 125° or less, 120° or less, 115° or less, 110° or less, 105° or less, 100° or less, 95° or less, 90° or less, 85° or less, 80° or less, 75° or less, 70° or less, 65° or less, 60° or less, 55° or less, or 50° or less). The included angle can range from any of the minimum values described above to any of the maximum values described above. For example, the included angle between the first principle axis and the second principle axis can be from 45° to 135° (e.g., from 45° to 90°, from 90° to 135°, from 45° to 60°, from 60° to 75°, from 75° to 900° from 90° to 105°, from 105° to 120°, from 120° to 135°, from 80° to 100°, or from 60° to 120°). In some examples, the included angle is 90°.

The size (e.g., characteristic dimension and/or thickness), shape, and/or composition of the plurality of plasmonic particles; the separation between each plasmonic particle within the array (e.g., the length of the first principle axis and/or the second principle axis); or combinations thereof can be selected in view of a variety of factors. In some examples, the size (e.g., characteristic dimension and/or thickness), shape, and/or composition of the plurality of plasmonic particles can be selected to maximize the electromagnetic field enhancement between the plasmonic particles along the first principle axis and/or the second principle axis. For example, the size (e.g., characteristic dimension and/or thickness), shape, and/or composition of the plurality of plasmonic particles; the separation between each plasmonic particle within the array (e.g., the length of the first principle axis and/or the second principle axis); or combinations thereof can be selected such that the intensity of an incident electromagnetic field is enhanced by a factor of 5 or more by the plurality of plasmonic particles (e.g., 10 or more, 20 or more, 30 or more, 40 or more, 50 or more, 60 or more 70 or more, 80 or more, 90 or more, or 100 or more). In some examples, the size (e.g., characteristic dimension and/or thickness), shape, and/or composition of the plurality of plasmonic particles; the separation between each plasmonic particle within the array (e.g., the length of the first principle axis and/or the second principle axis); or combinations thereof can be selected to give a desired array plasmon energy. In some examples, the size (e.g., characteristic dimension and/or thickness), shape, and/or composition of the plurality of plasmonic particles; the separation between each plasmonic particle within the array (e.g., the length of the first principle axis and/or the second principle axis); or combinations thereof can be selected such that the array plasmon energy overlaps with at least a portion of the electromagnetic radiation used to illuminate the nanostructured photonic material and/or such that the array plasmon energy does not substantially overlap with the hybrid plasmon waveguide mode.

The nanostructured photonic materials further comprises a waveguide layer disposed on the array and the first surface. The waveguide layer is disposed on the array and the first surface such that the array is encapsulated by the substrate and the waveguide layer (e.g., the array is sandwiched between the waveguide layer and the substrate, and the array is at least partially embedded within the waveguide layer, the substrate, or a combination thereof). The waveguide layer can have a refractive index that is lower or higher than the refractive index of the substrate.

The waveguide layer is optically coupled to the array and has an average thickness defining a hybrid plasmon waveguide mode. As used herein, "optically coupled" with respect to the array and the waveguide layer indicate that the waveguide layer is positioned with respect to the array such that incident light can strike the array and the waveguide layer, wherein when the light includes one or more wavelengths appropriate to excite the hybrid plasmon waveguide mode, the incident light can thereby exciting the hybrid plasmon waveguide mode. In some examples, the array plasmon energy does not substantially overlap with the hybrid plasmon waveguide more.

The waveguide layer can, for example, have an average thickness of 100 nm or more (e.g., 110 nm or more, 120 nm or more, 130 nm or more, 140 nm or more, 150 nm or more, 160 nm or more, 170 nm or more, 180 nm or more, 190 nm or more, 200 nm or more, 210 nm or more, 220 nm or more, 230 nm or more, 240 nm or more, 250 nm or more, 260 nm or more, 270 nm or more, 280 nm or more, or 290 nm or more). In some examples, the waveguide layer can have an average thickness of 300 nm or less (e.g., 290 nm or less, 280 nm or less, 270 nm or less, 260 nm or less, 250 nm or less, 240 nm or less, 230 nm or less, 220 nm or less, 210 nm or less, 200 nm or less, 190 nm or less, 180 nm or less, 170 nm or less, 160 nm or less, 150 nm or less, 140 nm or less, 130 nm or less, 120 nm or less, or 110 nm or less). The average thickness of the waveguide layer can range from any of the minimum values described above to any of the maximum values described above. For example, the waveguide layer can have an average thickness of from 100 nm to 300 nm (e.g., from 100 nm to 200 nm, from 200 nm to 300 nm, from 100 nm to 120 nm, from 120 nm to 140 nm, from 140 nm to 160 nm, from 160 nm to 180 nm, from 180 nm to 200 nm, from 200 nm to 220 nm, from 220 nm to 240 nm, from 240 nm to 260 nm, from 260 nm to 280 nm, from 280 nm to 300 nm, or from 120 nm to 280 nm). The thickness of the waveguide layer can be selected in view of a variety of factors. In some examples, the thickness of the waveguide layer can be selected such that the hybrid plasmon waveguide mode overlaps with at least a portion of the electromagnetic radiation used to illuminate the nanostructured photonic material; such that the hybrid plasmon waveguide mode does not substantially overlap with the array plasmon energy; such that the hybrid plasmon waveguide mode at least partially overlaps with the second optical state of the photochrome; such that the hybrid plasmon waveguide mode does not substantially overlap with the first optical state of the photochrome; or a combination thereof.

The waveguide layer comprises a photochrome dispersed within a matrix material, and the photochrome exhibits a first optical state and a second optical state. As used herein, a "photochrome" is any species that exhibits photochromism. Photochromism is the transformation of a chemical species between two forms by the absorption of electromagnetic radiation, where the two forms have different absorption spectra. In some examples, photochromism can be described as a change of color upon exposure to light. The second optical state of the photochrome at least partially overlaps with the hybrid plasmon waveguide mode, such that the waveguide energy mode exhibits Rabi splitting when the photochromic compound is in the second optical state. In some examples, the second optical state of the photochrome substantially overlaps with the hybrid plasmon waveguide mode. In some examples, the first optical state of the photochrome does not substantially overlap with the hybrid plasmon waveguide mode. In some examples, the first optical state of the photochrome is substantially optically transparent. Examples of photochromes include, but are not limited to, anthracene dimers, azobenzenes, bacteriorhodopsin, diarylethyenes, dihydroazulene, furyl fulgide, hexaarylbiimidazole, napthopyran, napthacene quinone, phenoxynaphthacene quinone, phytochrome, retinal, rhodopsin, ruthenium sulfoxide coordination compounds, silver halides (e.g., silver chloride, silver bromide, silver iodide, silver fluoride), sodalite, sodium nitroprusside coordination compounds, spiropyrans, spirooxazines, stilbene derivatives, tetracene, thioindigo, yttrium hydride, zinc halides, and combinations thereof. In some examples, the photochrome comprises spiropyran.

The photochrome can be selected in view of a variety of factors. In some examples, the photochrome can be selected such that the second optical state overlaps with at least a portion of the electromagnetic radiation used to illuminate the nanostructured photonic material; such that the second optical state of the photochrome does not substantially overlap with the array plasmon energy; such that the second optical state of the photochrome at least partially overlaps with the hybrid plasmon waveguide mode; such that first optical state of the photochrome does not substantially overlap with the hybrid plasmon waveguide mode; or a combination thereof.

The matrix material can comprise any suitable material for dispersing the photochrome. For example, the matrix material can comprise a polymer. Examples of polymers suitable for the matrix materials include, but are not limited to, poly(methyl methacrylate) (PMMA), polyamide, polycarbonate, polyester, polypropylene, polytetrafluoroethylene, polydimethyl siloxane (PDMS), polypropylene, acrylonitrile butadiene styrene (ABS), polylactic acid, polybenzimidazole, polyether sulfone, polyether ether ketone (PEEK), polyethylene, polyetherimide, polyphenylene oxide, polyphenylene sulfide, polystyrene, polybutylene, cellulose acetate, ethylene-vinyl acetate, ethylene tetrafluoroethylene, ethylene chlorotrifluoroethylene, perfluoroalkoxy alkanes, perfluoro ethers, poly(3-hydroxybutyrate-co-3-hydroxyvalerate), polyvinylidene fluoride, polysulfone, polyphthalamide, polyhydroxybutyrate, polyacetal, polyketone, polyhydroxyalkanoate, polyglycolide, polyethylene terephthalate, polyetherketoneketone (PEKK), polycaprolactone, polybutylene terephthalate, polybutylene succinate, polybutadiene, polyarvlether ketone, polyamide-imide, polyacrylonitrile, polyphenylene sulfide, polyimide, and combinations thereof. In some examples, the matrix material comprises polymethyl methacrylate (PMMA). In some examples, the substrate and the matrix material can both comprise a polymer. In some examples, the substrate and the matrix material can be the same material. In some examples, the substrate can be the same material as the waveguide layer.

Methods of Making

Also disclosed herein are methods of making the nanostructured photonic materials described herein. For example, the nanostructured photonic materials described herein can be made by a method comprising depositing the plurality of plasmonic particles on the first surface of the substrate, thereby forming the array, dispersing the photochrome in the matrix material, thereby forming a mixture; and depositing the mixture on the array and the first surface, thereby forming the waveguide layer.

Depositing the plurality of plasmonic particles can, for example, comprise lithographic deposition, such as electron beam lithography, nanoimprinting, focused ion beam lithography, or a combination thereof.

Depositing the mixture can comprise, in some examples, printing, spin coating, drop-casting, zone casting, dip coating, blade coating, spraying, vacuum filtration, slot die coating, curtain coating, or combinations thereof.

Methods of Use

Also disclosed herein are methods of use of the nanostructured photonic materials described herein. In some examples, the method of use comprises using the nanostructured photonic material as an optically rewriteable waveguide. The method can comprise illuminating a first location of the waveguide layer with light configured to switch the photochrome proximate the first location from the first optical state to the second optical state, thereby inducing Rabi splitting in the hybrid plasmon waveguide mode and forming a nanostructured photonic waveguide proximate the first location. As used herein, "a first location" and "the first location" are meant to include any number of locations in any arrangement on the waveguide layer. Thus, for example "a first location" includes one or more first locations. In some embodiments, the first location can comprise a plurality of locations. In some embodiments, the first locations can comprise a plurality of locations arranged in an ordered array.

The light can, for example, be provided by a light source. The light source can be any type of light source. Examples of suitable light sources include natural light sources (e.g., sunlight) and artificial light sources (e.g., incandescent light bulbs, light emitting diodes, gas discharge lamps, arc lamps, lasers, etc.). In some examples, the light source is configured to illuminate a mirror, the mirror being configured to reflect the light from the light source to illuminate the first location of the waveguide layer. In some examples, the mirror can comprise a plurality of mirrors, such as an array of micromirrors (e.g., a digital micromirror device).

The Rabi splitting can, for example, have a splitting energy of 250 millielectronvolts (meV) or more (e.g., 300 meV or more, 350 meV or more, 400 meV or more, 450 meV or more, 500 meV or more, 550 meV or more, 600 meV or more, 700 meV or more, 800 meV or more, 900 meV or more, 1000 meV or more, 1100 meV or more, 1200 meV or more, 1300 meV or more, 1400 meV or more, 1500 meV or more, 1750 meV or more, 2000 meV or more, 2250 meV or more, 2500 meV or more, 2750 meV or more, 3000 meV or more, 3250 meV or more, 3500 meV or more, or 3750 meV or more). In some examples, the Rabi splitting can have a splitting energy of 4000 meV or less (e.g., 3750 meV or less, 3500 meV or less, 3250 meV or less, 3000 meV or less, 2750 meV or less, 2500 meV or less, 2250 meV or less, 2000 meV or less, 1750 meV or less, 1500 meV or less, 1400 meV or less, 1300 meV or less, 1200 meV or less, 1100 meV or less, 1000 meV or less, 900 meV or less, 800 meV or less, 700 meV or less, 600 meV or less, 550 meV or less, 500 meV or less, 450 meV or less, 400 meV or less, 350 meV or less, or 300 meV or less). The Rabi splitting energy can range from any of the minimum values described above to any of the maximum values described above. For example, the Rabi splitting can have a splitting energy of from 250 meV to 4000 meV (e.g., from 250 meV to 2000 meV, from 2000 meV to 4000 meV, from 250 meV to 1000 meV, from 1000 meV to 1750 meV, from 1750 meV to 2500 meV, from 2500 meV to 3250 meV, from 325° to 4000 meV, from 400 meV to 700 meV, or from 300 meV to 3000 meV).

In some examples, the methods can further comprise illuminating the first location of the waveguide layer with light configured to switch the photochrome proximate the first layer from the second optical state to the first optical state, thereby erasing the photonic waveguide proximate the first location. The light can, for example, be provided by a light source. The light source can be any type of light source. Examples of suitable light sources include natural light sources (e.g., sunlight) and artificial light sources (e.g., incandescent light bulbs, light emitting diodes, gas discharge lamps, arc lamps, lasers, etc.). In some examples, the light source is configured to illuminate a mirror, the mirror being configured to reflect the light from the light source to illuminate the first location of the waveguide layer. In some examples, the mirror can comprise a plurality of mirrors, such as an array of micromirrors (e.g., a digital micromirror device).

In some examples, the methods can further comprise illuminating a second location of the waveguide layer with light configured to switch the photochrome proximate the second location from the first optical state to the second optical state, thereby inducing Rabi splitting in the hybrid plasmon waveguide mode and forming a nanostructured photonic waveguide proximate the second location. As used herein. "a second location" and "the second location" are meant to include any number of locations in any arrangement on the waveguide layer. Thus, for example "a second location" includes one or more second locations. In some embodiments, the second location can comprise a plurality of locations. In some embodiments, the second location can comprise a plurality of locations arranged in an ordered array. In some examples, the nanostructured photonic materials, the substrate, the array, the waveguide layer, the light source, the mirror, or a combination thereof can be translocated to illuminate the second location. As used herein translocating refers to any type of movement about any axis (e.g., rotation, translation, etc.) In other words, as used herein, translocation refers to a change in position and/or orientation.

The optically rewriteable waveguide can be written in any desired design. The optically rewriteable waveguide can be written, erased, and rewritten any suitable number of times.

Systems

Also disclosed herein are systems comprising the nanostructured photonic materials described herein. Referring now to FIG. 1, the systems 100 can comprise a nanostructured photonic material 102 comprising a substrate 104 having a first surface 106, an array 108 comprising a plurality of spaced-apart plasmonic particles 110 disposed on the first surface 106 of the substrate 104, a waveguide layer 112 disposed on the array 108 and the first surface 106, wherein the waveguide layer 112: is optically coupled to the array 108, comprises a photochrome dispersed within a matrix material, and has an average thickness defining a hybrid plasmon waveguide mode, wherein the photochrome exhibits a first optical state and a second optical state, and wherein the second optical state of the photochrome at least partially overlaps with the hybrid plasmon waveguide mode; and a first light source 114 configured to illuminate the nanostructured photonic material 102.

The first light source 114 can be any type of light source. Examples of suitable light sources include natural light sources (e.g., sunlight) and artificial light sources (e.g., incandescent light bulbs, light emitting diodes, gas discharge lamps, arc lamps, lasers, etc.). In some examples, the first light source 114 comprises an artificial light source. In some examples, the first light source 114 comprises a white light source.

In some examples, the systems 100 can further comprise a means for translocating for translocating the nanostructured photonic material 102, the substrate 104, the array 108, the waveguide layer 112, the first light source 114, or a combination thereof. In some examples, the system 100 is aligned such that array 108 is disposed between the waveguide layer 112 and the first light source 114. As used herein translocating refers to any type of movement about any axis (e.g., rotation, translation, etc.) In other words, as used herein, translocation refers to a change in position and/or orientation.

Figure 2:
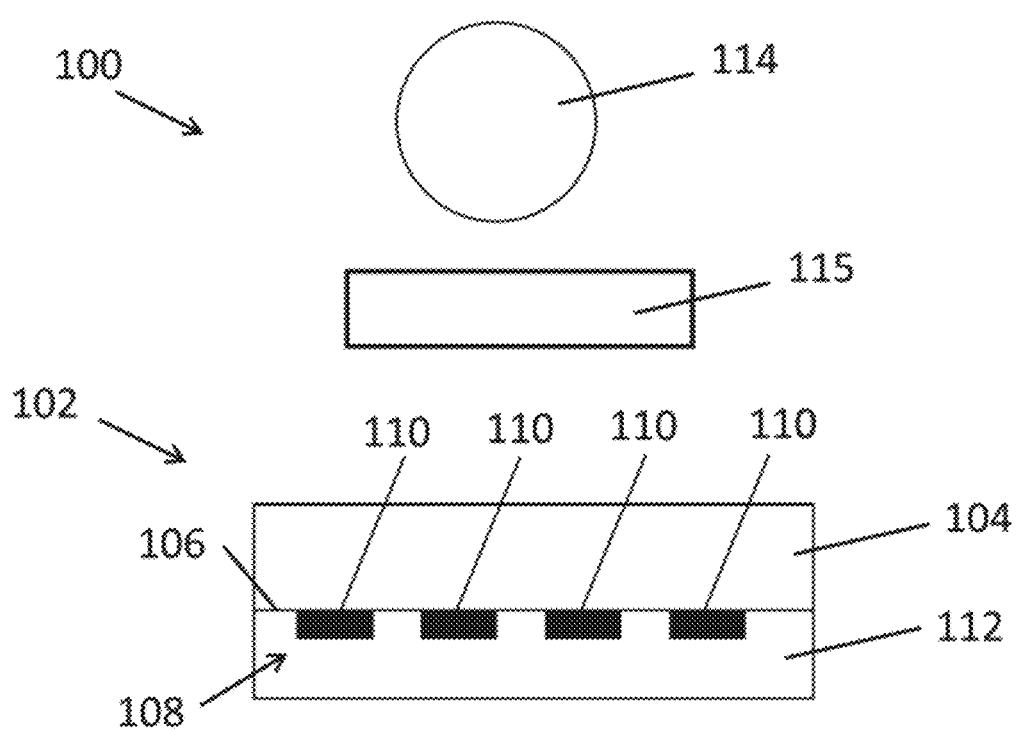
FIG. 2 is a schematic of an exemplary system as disclosed herein.

The system 100 can, in some examples, further comprise a polarizer 115 configured to polarize the light from the first light source 114. The polarizer 115 can, for example, comprise a linear polarizer or a circular polarizer. Referring now to FIG. 2, the system 100 can, for example, be aligned such that the first light source 114 is above the polarizer 115 and the nanostructured photonic material 102 is below the polarizer 115, with the array 108 being disposed between the waveguide layer 112 and the first light source 114.

Figure 3:
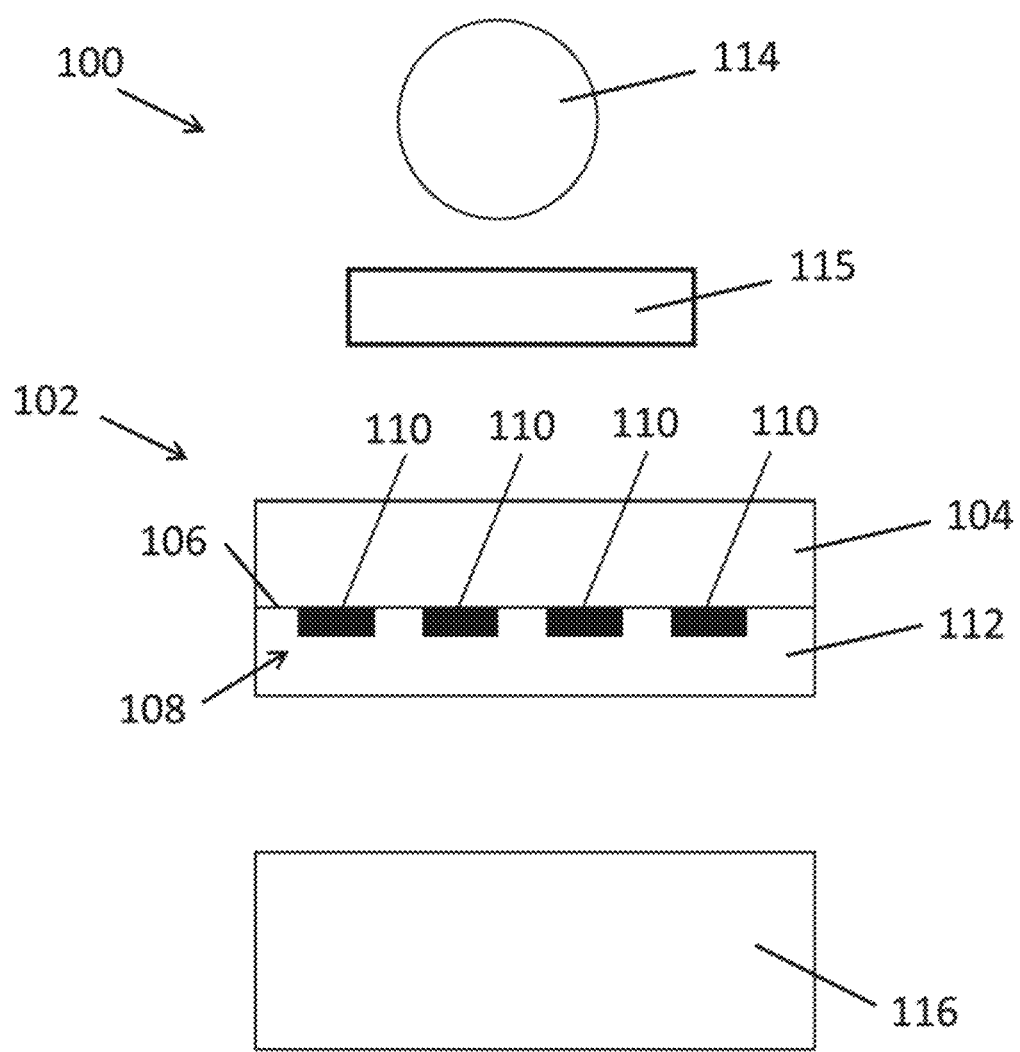
FIG. 3 is a schematic of an exemplary system as disclosed herein.

The system 100 can, in some examples, further comprise an instrument 116 configured to capture an electromagnetic signal from the nanostructured photonic material 102. Referring now to FIG. 3, the system 100 can, for example, be aligned such that the first light source 114 is above the polarizer 115, the nanostructured photonic material 102 is below the polarizer 115, with the array 108 being disposed between the waveguide layer 112 and the first light source 114, and the instrument 116 is below the nanostructured photonic material 102. The instrument 116 can, for example, comprise a camera, an optical microscope, an electron microscope, a spectrometer, or combinations thereof. Examples of spectrometers include, but are not limited to, Raman spectrometers, UV-vis absorption spectrometers, IR absorption spectrometers, fluorescence spectrometers, reflectance spectrometers, and combinations thereof.

Figure 4:
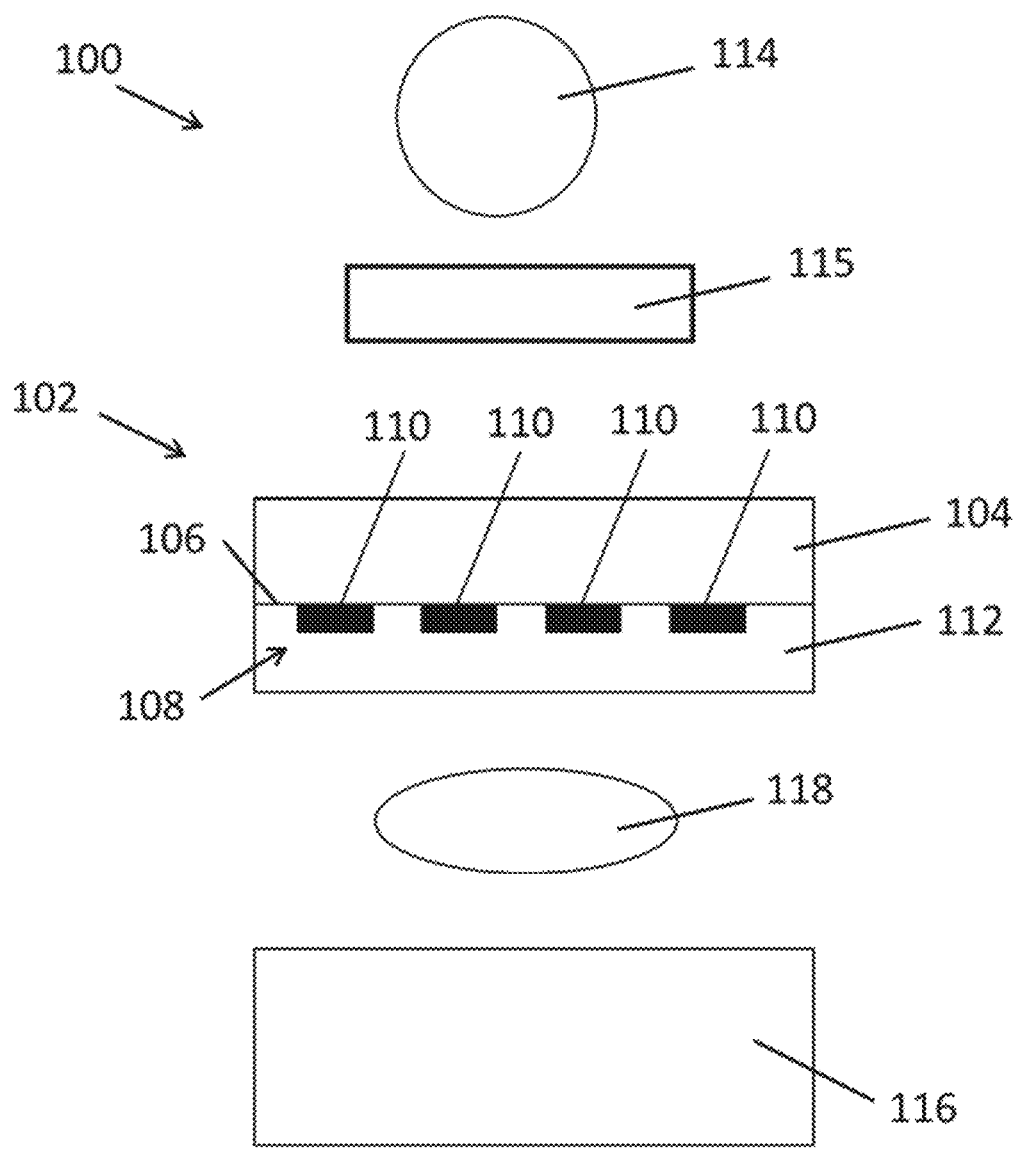
FIG. 4 is a schematic of an exemplary system as disclosed herein.

In some examples, the system 100 can further comprise a first lens 118. Referring now to FIG. 4, the system 100 can, for example, be aligned such that the first light source 114 is above the polarizer 115, the nanostructured photonic material 102 is below the polarizer 115, with the array 108 being disposed between the waveguide layer 112 and the first light source 114, the first lens 118 is below the nanostructured photonic material 102, and the instrument 116 is below the first lens 118. The first lens can be any type of lens, such as a simple lens, a compound lens, a spherical lens, a toric lens, a biconvex lens, a piano-convex lens, a plano-concave lens, a negative meniscus lens, a positive meniscus lens, a biconcave lens, a converging lens, a diverging lens, a cylindrical lens, a Fresnel lens, a lenticular lens, or a gradient index lens.

Figure 5:
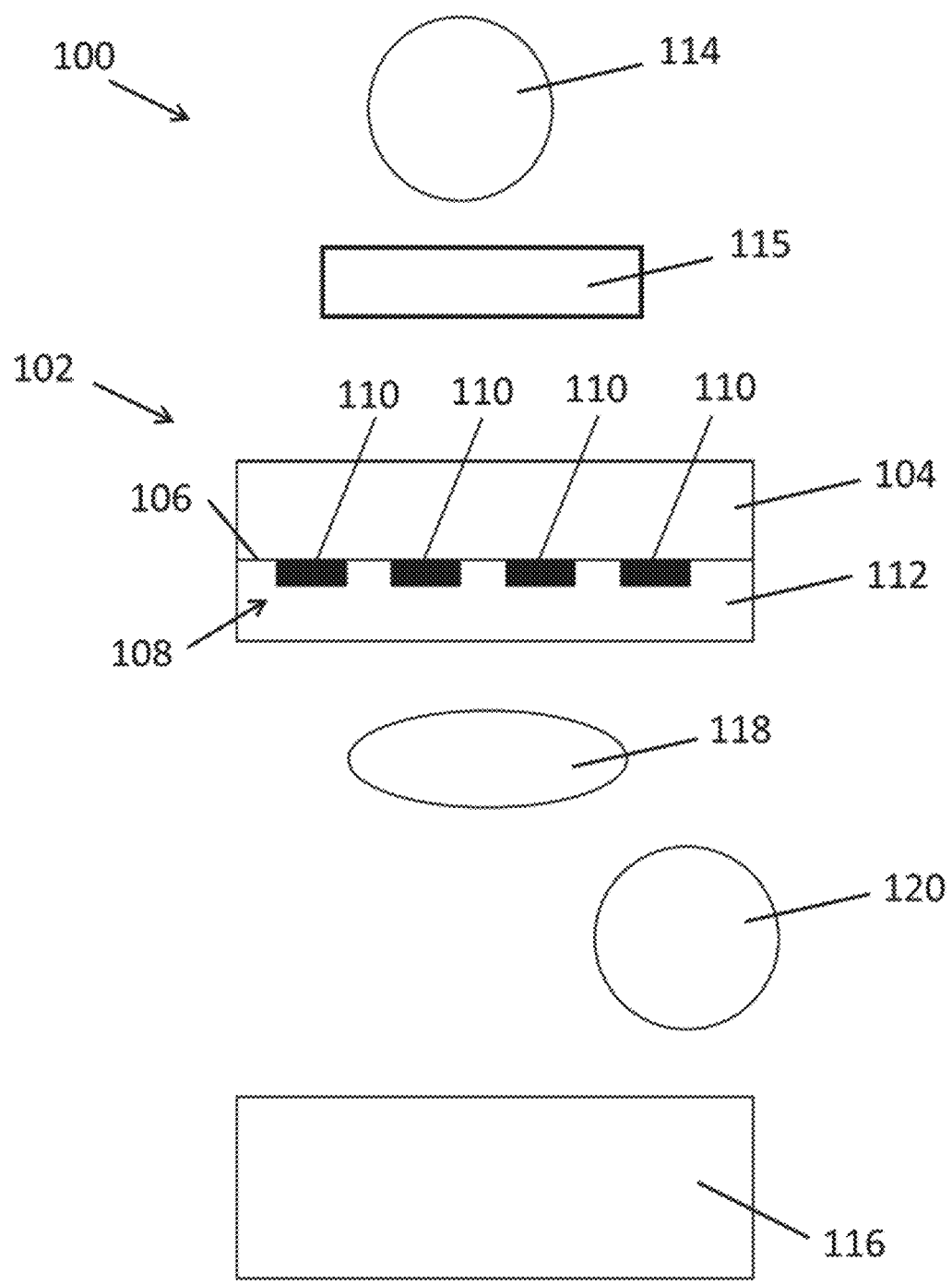
FIG. 5 is a schematic of an exemplary system as disclosed herein.

In some examples, the system 100 can further comprise a second light source 120, the second light source 120 being configured to illuminate the nanostructured photonic material 102 at a first location. Referring now to FIG. 5, the system 100 can, for example, be aligned such that the waveguide layer 112 is disposed between the second light source 120 and the array 108. In some examples, the system 100 can be aligned such that the first light source 114 is above the polarizer 115, the nanostructured photonic material 102 is below the polarizer 115, with the array 108 being disposed between the waveguide layer 112 and the first light source 114, the first lens 118 is below the nanostructured photonic material 102, the instrument 116 is below the first lens 118, and the second light source 120 is below the first lens 118. In some examples, the second light source 120 is configured to illuminate the nanostructured photonic material 102 at the first location thereby switching the photochrome proximate to the first location from the first optical state to the second optical state. The second light source 120 can be any type of light source. Examples of suitable light sources include natural light sources (e.g., sunlight) and artificial light sources (e.g., incandescent light bulbs, light emitting diodes, gas discharge lamps, arc lamps, lasers, etc.). In some examples, the second light source 120 comprises an artificial light source. In some examples, the second light source 120 comprises a UV light source. In some examples, the system 100 can further comprise a means for translocating the second light source 120.

Figure 6:
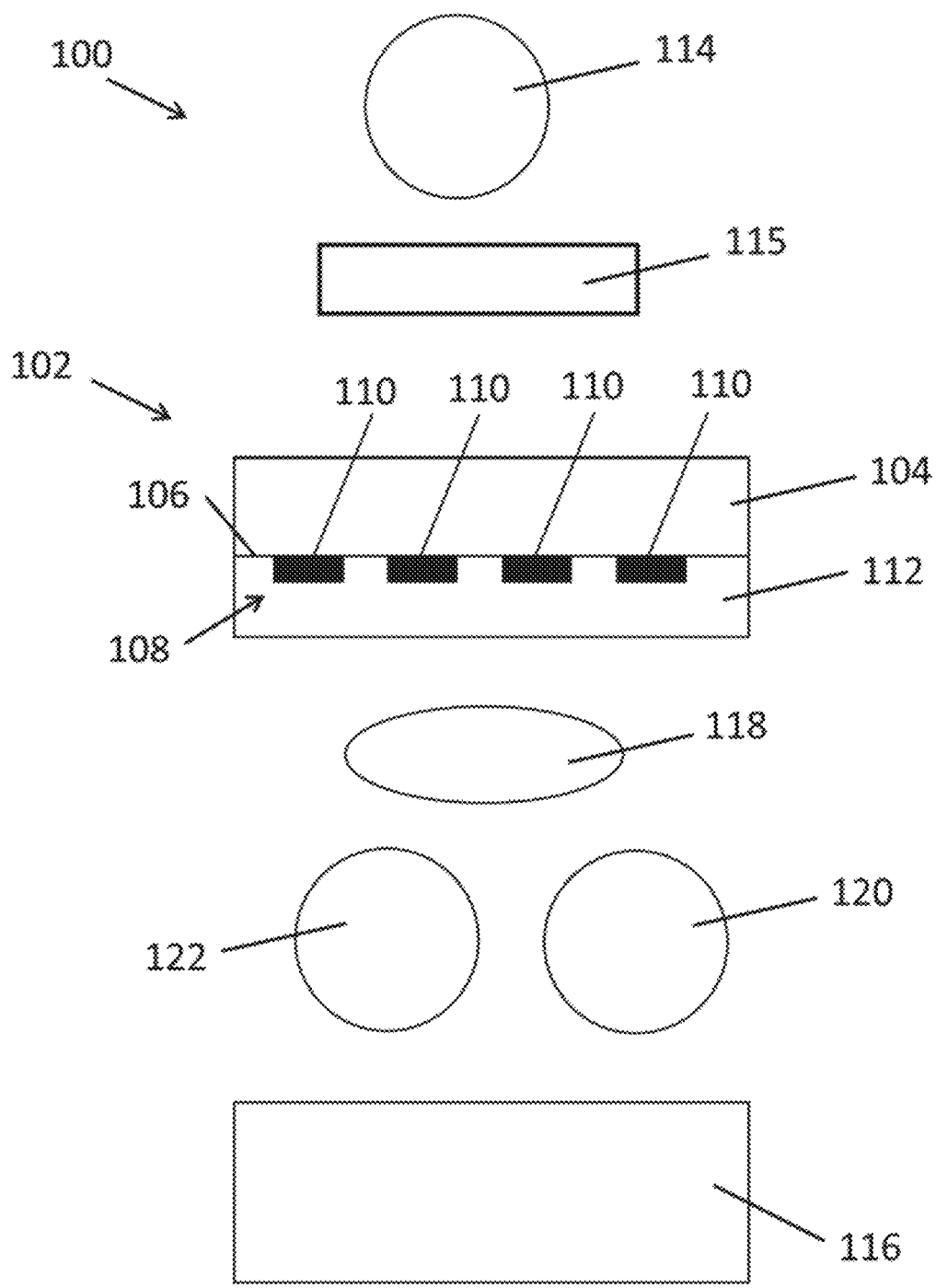
FIG. 6 is a schematic of an exemplary system as disclosed herein.

The system 100 can, in some examples, further comprise a third light source 122 configured to illuminate the nanostructured photonic material 102 at the first location. Referring now to FIG. 6, the system 100 can, for example, be aligned such that the waveguide layer 112 is disposed between the third light source 122 and the array 108. In some examples, the system 100 is aligned such that the first light source 114 is above the polarizer 115, the nanostructured photonic material 102 is below the polarizer 115, with the array 108 being disposed between the waveguide layer 112 and the first light source 114, the first lens 118 is below the nanostructured photonic material 102, the instrument 116 is below the first lens 118, the second light source 120 is below the first lens 118, and the third light source 122 is below the first lens 118. In some examples, the third light source 122 is configured to illuminate the nanostructured photonic material 102 at the first location thereby switching the photochrome proximate to the first location from the second optical state to the first optical state. The third light source 122 can be any type of light source. Examples of suitable light sources include natural light sources (e.g., sunlight) and artificial light sources (e.g., incandescent light bulbs, light emitting diodes, gas discharge lamps, arc lamps, lasers, etc.). In some examples, the third light source 122 can comprise an artificial light source. In some examples, the third light source 122 can comprise a green light source (e.g., a light source that provides light in the green region of the visible spectrum). In some examples, the system 100 can further comprise a means for translocating the third light source 122.

Figure 7:
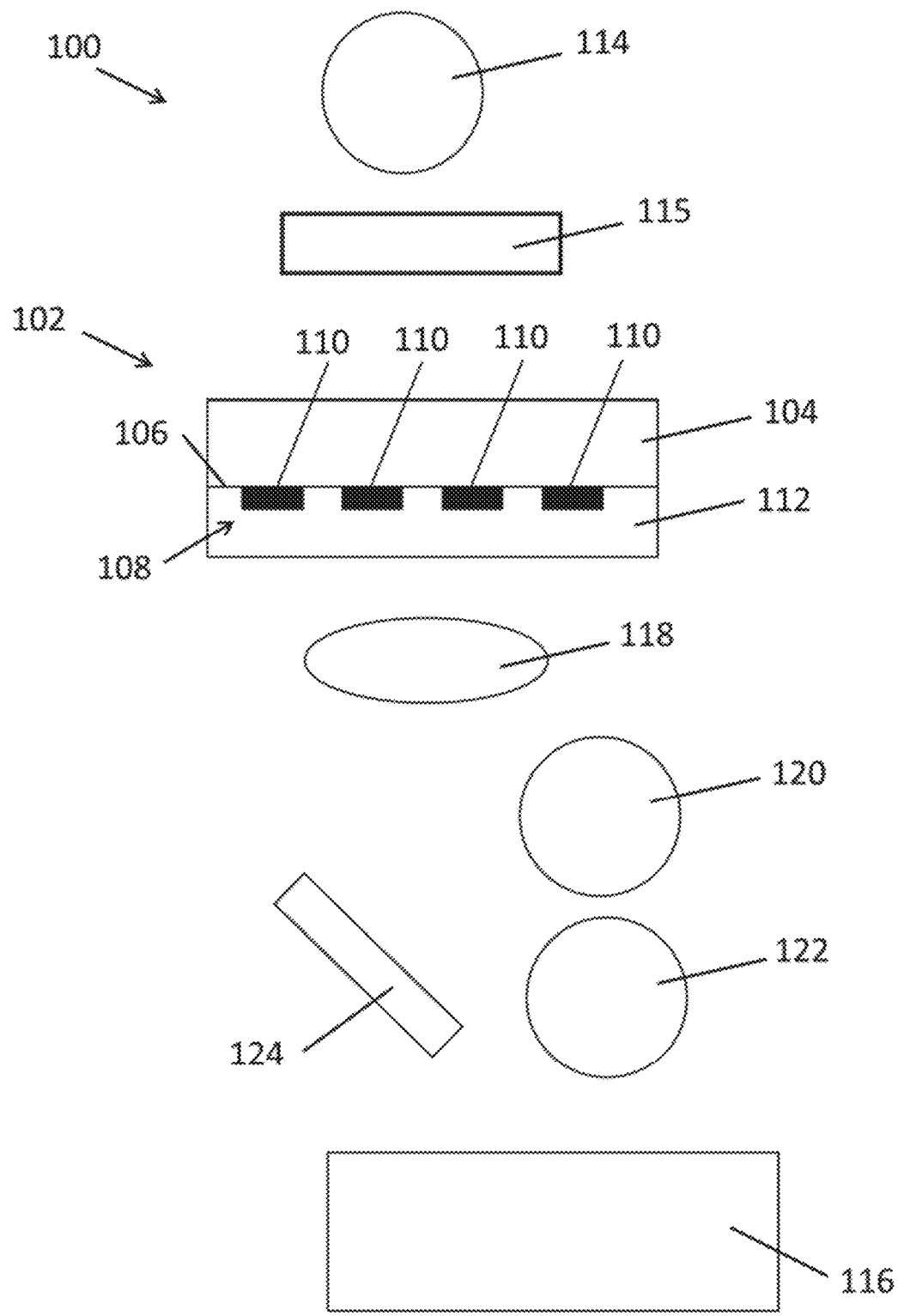
FIG. 7 is a schematic of an exemplary system as disclosed herein.

The system 100 can, in some examples, further comprise a mirror 124. Referring now to FIG. 7, the system 100 can, for example, be aligned such that the second light source 120 and/or the third light source 122 is configured to illuminate the mirror 124 and the mirror 124 is configured to reflect the electromagnetic radiation from the light source to illuminate the first location of the nanostructured photonic material 102. The mirror 124 can, in some examples, comprise a plurality of mirrors. The plurality of mirror can, for example, comprise a digital micromirror device. In some examples, the systems 100 can further comprise a means for translocating the mirror 124.

In some examples, the second light source 120 and the third light source 122 can be a single light source.

Figure 8:
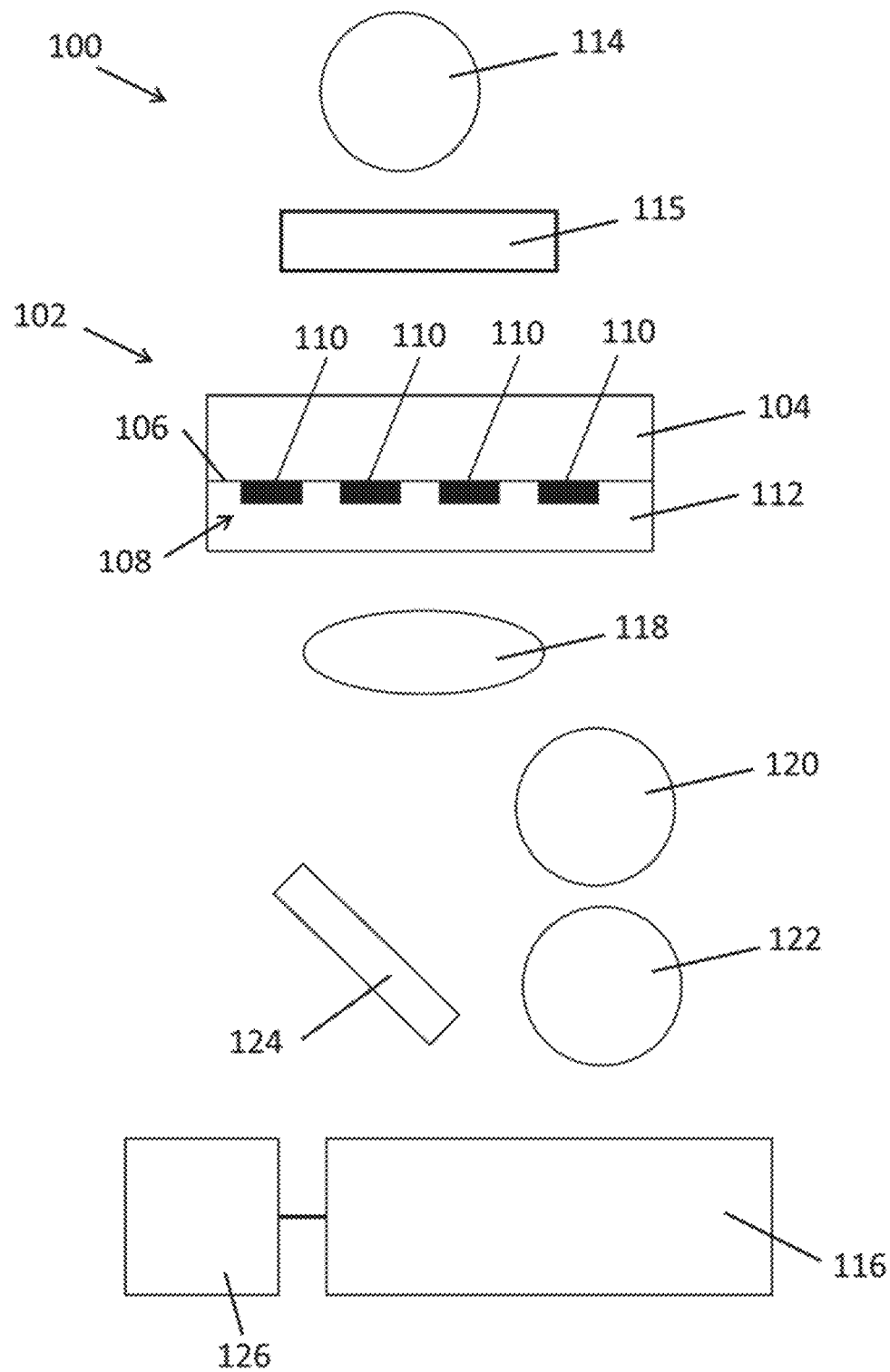
FIG. 8 is a schematic of an exemplary system as disclosed herein.

In some examples, the systems 100, can further comprise a computing device 126 configured to receive and process electromagnetic signals from the instrument 116, for example as shown in FIG. 8.

Figure 9:
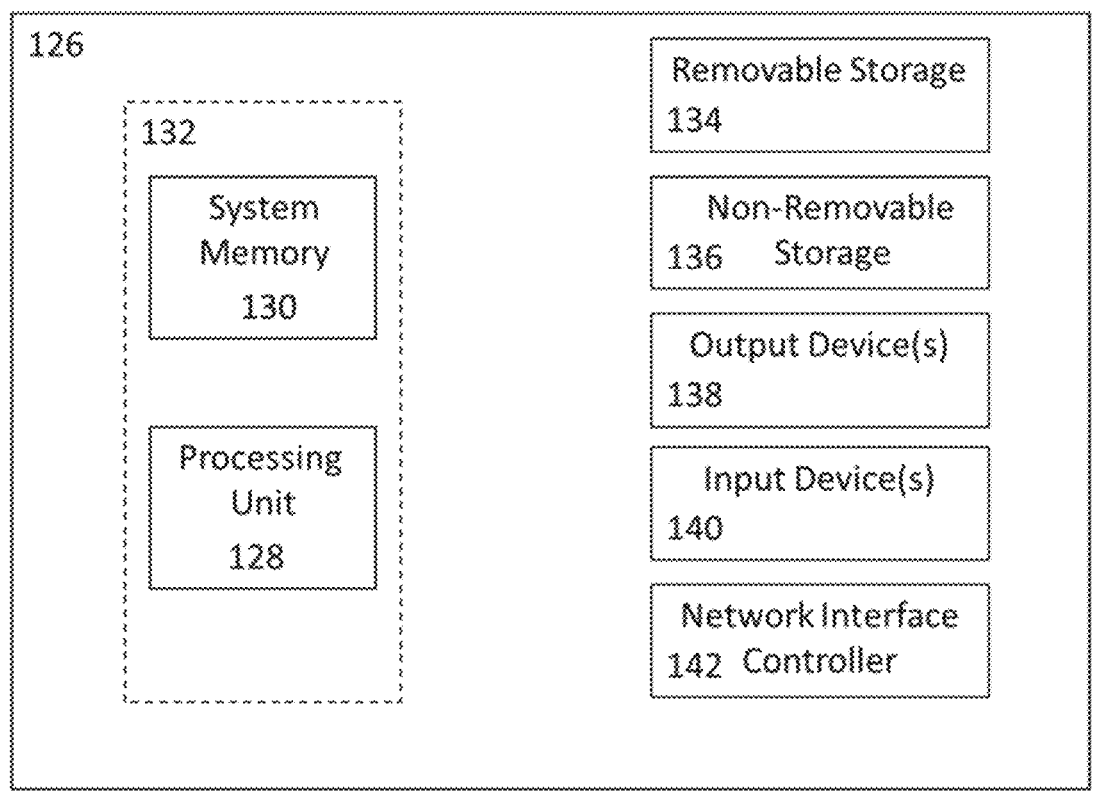
FIG. 9 is a schematic of an exemplary computing device.

FIG. 9 illustrates an example computing device 126 upon which examples disclosed herein may be implemented. The computing device 126 can include a bus or other communication mechanism for communicating information among various components of the computing device 126. In its most basic configuration, computing device 126 typically includes at least one processing unit 128 (a processor) and system memory 130. Depending on the exact configuration and type of computing device, system memory 130 may be volatile (such as random access memory (RAM)), non-volatile (such as read-only memory (ROM), flash memory, etc.), or some combination of the two. This most basic configuration is illustrated in FIG. 9 by a dashed line 132. The processing unit 128 may be a standard programmable processor that performs arithmetic and logic operations necessary for operation of the computing device 126.

The computing device 126 can have additional features/functionality. For example, computing device 126 may include additional storage such as removable storage 134 and non-removable storage 136 including, but not limited to, magnetic or optical disks or tapes. The computing device 126 can also contain network connection(s) 142 that allow the device to communicate with other devices. The computing device 126 can also have input device(s) 140 such as a keyboard, mouse, touch screen, antenna or other systems configured to communicate with the camera in the system described above, etc. Output device(s) 138 such as a display, speakers, printer, etc. may also be included. The additional devices can be connected to the bus in order to facilitate communication of data among the components of the computing device 126.

The processing unit 128 can be configured to execute program code encoded in tangible, computer-readable media. Computer-readable media refers to any media that is capable of providing data that causes the computing device 126 (i.e., a machine) to operate in a particular fashion. Various computer-readable media can be utilized to provide instructions to the processing unit 128 for execution. Common forms of computer-readable media include, for example, magnetic media, optical media, physical media, memory chips or cartridges, a carrier wave, or any other medium from which a computer can read. Example computer-readable media can include, but is not limited to, volatile media, non-volatile media and transmission media. Volatile and non-volatile media can be implemented in any method or technology for storage of information such as computer readable instructions, data structures, program modules or other data and common forms are discussed in detail below. Transmission media can include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 128 can execute program code stored in the system memory 130. For example, the bus can carry data to the system memory 130, from which the processing unit 128 receives and executes instructions. The data received by the system memory 130 can optionally be stored on the removable storage 134 or the non-removable storage 136 before or after execution by the processing unit 128.

The computing device 126 typically includes a variety of computer-readable media. Computer-readable media can be any available media that can be accessed by device 118 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 130, removable storage 134, and non-removable storage 136 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 126. Any such computer storage media can be part of computing device 126.

It should be understood that the various techniques described herein can be implemented in connection with hardware or software or, where appropriate, with a combination thereof. Thus, the methods, systems, and associated signal processing of the presently disclosed subject matter, or certain aspects or portions thereof, can take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs can implement or utilize the processes described in connection with the presently disclosed subject matter, e.g., through the use of an application programming interface (API), reusable controls, or the like. Such programs can be implemented in a high level procedural or object-oriented programming language to communicate with a computer system. However, the program(s) can be implemented in assembly or machine language, if desired. In any case, the language can be a compiled or interpreted language and it may be combined with hardware implementations.

In certain examples, the system memory 130 comprises computer-executable instructions stored thereon that, when executed by the processor 128, cause the processor 128 to receive an electromagnetic signal from the instrument 116; process the electromagnetic signal to obtain a characteristic of the nanostructured photonic material 102; and output the characteristic of the nanostructured photonic material 102.

The analysis of signals captured by the instrument can be carried out in whole or in part on one or more computing device. For example, the system may comprise one or more additional computing device.

In some examples, the electromagnetic signal received by the processor from the instrument can comprise an image, a spectrum (e.g., Raman, UV-vis, IR, fluorescence, reflectance), a micrograph, or combinations thereof. The characteristic of the nanostructured photonic material can comprise, for example, the presence, location, composition, size, shape, and/or quantity of plasmonic particles comprising the array; the presence, location, and/or composition of the photochrome; the presence, location, and/or composition of the matrix material; the presence, location, and/or composition of the substrate; or combinations thereof. In some examples, the characteristic of the nanostructured photonic material can be monitored over time, for example, to identify that the photochrome has been switched from the first optical state to the second optical state, or vice-versa, and/or the effect of said switch.

Figure 10:
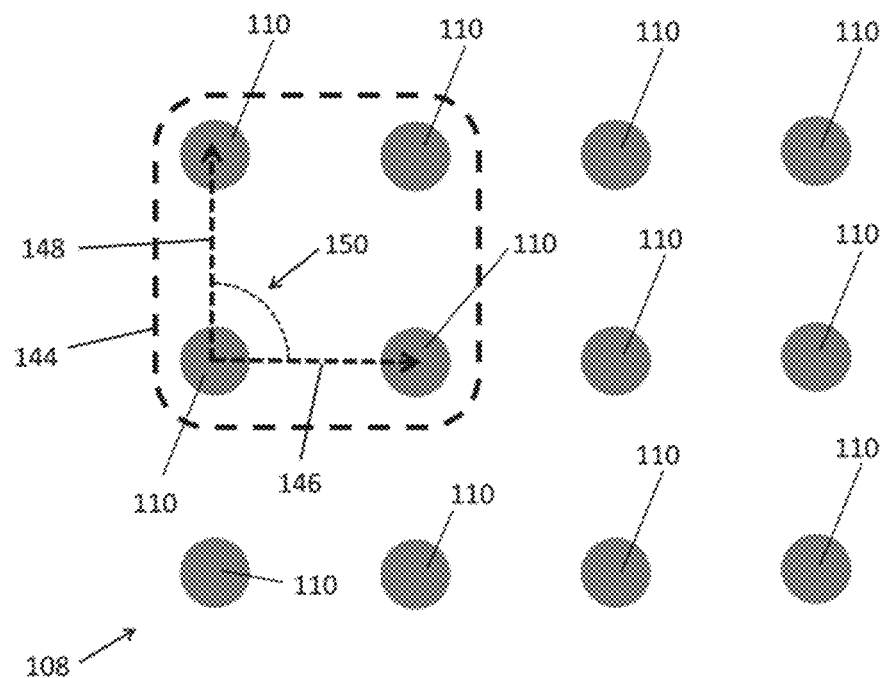
FIG. 10 is a schematic of an exemplary array.
Figure 11:
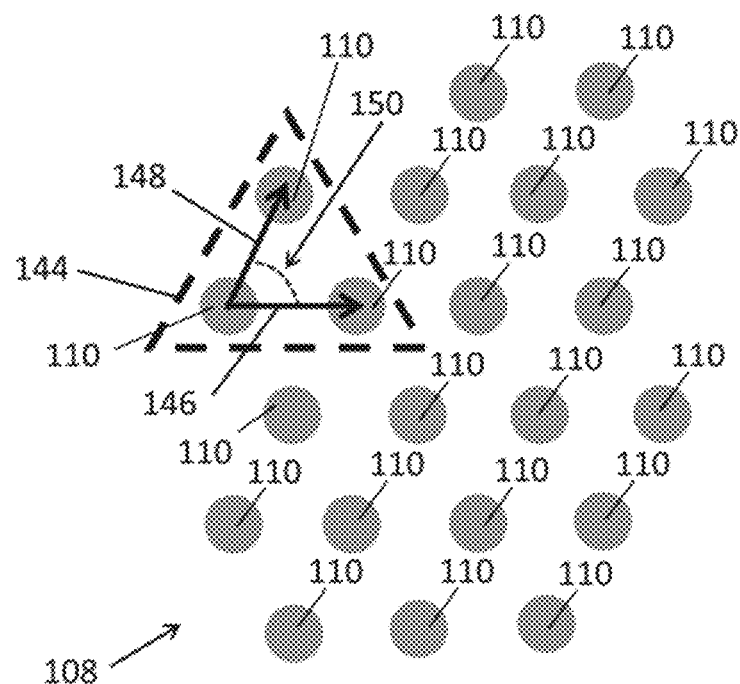
FIG. 11 is a schematic of an exemplary array.

Referring now to FIG. 10 and FIG. 11, in some examples, the array 108 is defined by a unit cell 144, the unit cell having: a first principle axis 146 and a second principle axis 148 with an included angle 150 between the first principle axis and the second principle axis; wherein the first principle axis 146 has a length that is the distance separating each plasmonic particle in the array 108 from its neighboring plasmonic particle (edge to edge) along the first principle axis 146; wherein the length of the first principle axis is two times the characteristic dimension of the plasmonic particles 110 or less; wherein the second principle axis has a length that is the distance separating each plasmonic particle in the array 108 from its neighboring plasmonic particle (edge to edge) along the second principle axis. Referring now to FIG. 10, in some examples, the unit cell 144 is in the shape of a rectangle. Referring now to FIG. 11, in some examples, the unit cell 144 is in the shape of a triangle.

In some examples, the systems 100 can include the polarizer 115, wherein the polarizer 115 is a linear polarizer configured to polarize the light from the first light source 114 along the direction of the first principle axis 146.

A number of embodiments of the invention have been described. Nevertheless, it will be understood that various modifications may be made without departing from the spirit and scope of the invention. Accordingly, other embodiments are within the scope of the following claims.

The examples below are intended to further illustrate certain aspects of the systems and methods described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of measurement conditions, e.g., component concentrations, temperatures, pressures and other measurement ranges and conditions that can be used to optimize the described process.

Example 1

Herein, photoswitchable Rabi splitting in the hybrid plasmon-waveguide modes supported by Al nanodisk arrays covered by a thin polymethyl methacrylate (PMMA) waveguide layer that is doped with spiropyran (SP)-based photochromic molecules is demonstrated. The hybrid plasmon-waveguide modes exhibit both subwavelength mode confinement with intense localized electric field and long-range light waveguiding. The hybrid plasmon-waveguide modes in the hybrid systems can couple strongly with molecular excitons, leading to Rabi splitting. By harnessing the photoswitchable configurations of the molecules. i.e., switching between the spiropyran closed form and open form-merocyanine (MC), the Rabi splitting can be reversibly controlled and all-optical light modulation can be achieved. Furthermore, optically rewritable waveguides are discussed that use the photoswitchable Rabi splitting in the hybrid plasmon-waveguide modes. The hybrid plasmon-waveguide modes with the photoswitchable Rabi splitting described herein have the advantages of low optical loss, subwavelength confinement of light, and reversible light modulation. The hybrid plasmon-waveguide modes with the photoswitchable Rabi splitting can be used for applications in both standalone active optical devices and lab-on-a-chip systems (Yang X et al. *Nano Lett.* 2011, 11, 321-328).

Figure 12:
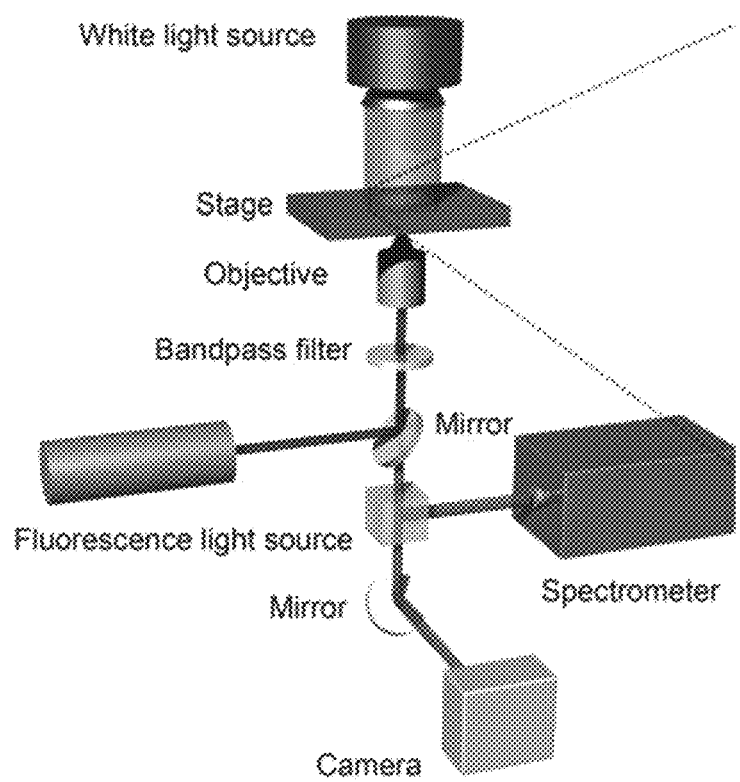
FIG. 12 is a schematic of the optical setup for the study of photoswitchable Rabi splitting between hybrid plasmon-waveguide modes and molecular excitons, as well as sample design and characterization.
Figure 13:
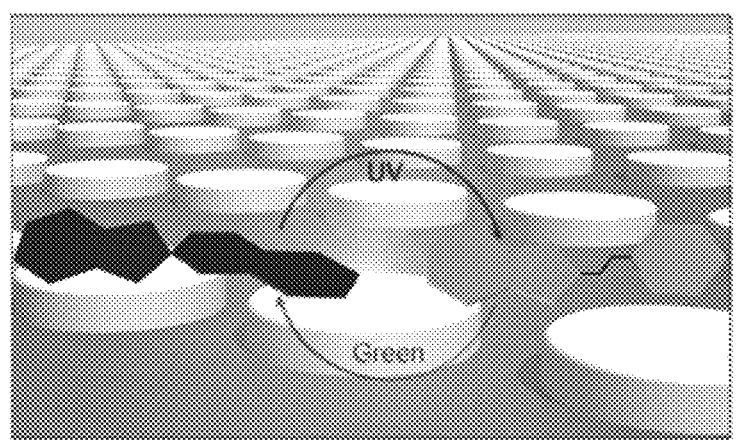
FIG. 13 is a schematic view of the sample of Al nanodisk arrays covered by PMMA thin films doped with spiropyran-based photochromic molecules. The photochromic molecules undergo reversible isomerization between their spiropyran form and merocyanine form upon alternative illumination of UV light and green light.

FIG. 12 shows a schematic of the optical setup for characterizing the photoswitchable Rabi splitting in the hybrid plasmon-waveguide modes. FIG. 13 shows a schematic of the sample comprising a glass substrate, Al nanodisk arrays, and PMMA thin film doped with spiropyran molecules. Aluminum was chosen as the plasmonic material because of its wide-range optical responses from ultraviolet to visible region, technical compatibility with current CMOS-based integrated circuits, abundance in the earth's crust, and high stability with passivation by oxide layer.

The samples were prepared by fabricating Al nanodisk arrays on glass substrates using electron beam lithography (EBL, 6000 FSE, JEOL) and electron beam deposition (Cooke Vacuum Products). A 2 nm Cr layer was used as an adhesion layer between the 30 nm Al layer and the glass substrate. An atomic force microscope (AFM, Park Systems) was employed for morphology characterization of the Al nanodisk arrays.

The regular Al nanodisk arrays were embedded in the PMMA waveguide layer (e.g., PMMA doped with spiropyran) at the glass-PMMA interface to hybridize localized surface plasmon resonances with propagating waveguides. It is known that an increase in the molecule concentration can enhance the Rabi splitting. However, the maximum concentration is limited by the solubility of spiropyran molecules in the organic solvent and PMMA and the higher concentration of molecules could result in the poor-quality PMMA films. Herein, the molecule concentration was chosen as per previous work (Dintinger J et al. *Adv. Mater.* 2006, 18, 1267-1270; Zheng Y B et al. *Nano Lett.* 2011, 11, 2061-2065). Specifically, spiropyran (SP, Sigma-Aldrich) molecules were mixed with PMMA (Sigma-Aldrich) with a weight ratio of 1:1 in chlorobenzene (2 wt % of spiropyran in chlorobenzene). The spiropyran doped PMMA mixture was spin-coated onto the Al nanodisk arrays at 2000 rpm for one minute. The thickness and dielectric function of the spiropyran-doped PMMA films were determined by ellipsometry (M-2000, J.A. Woollam Co.).

Figure 14:
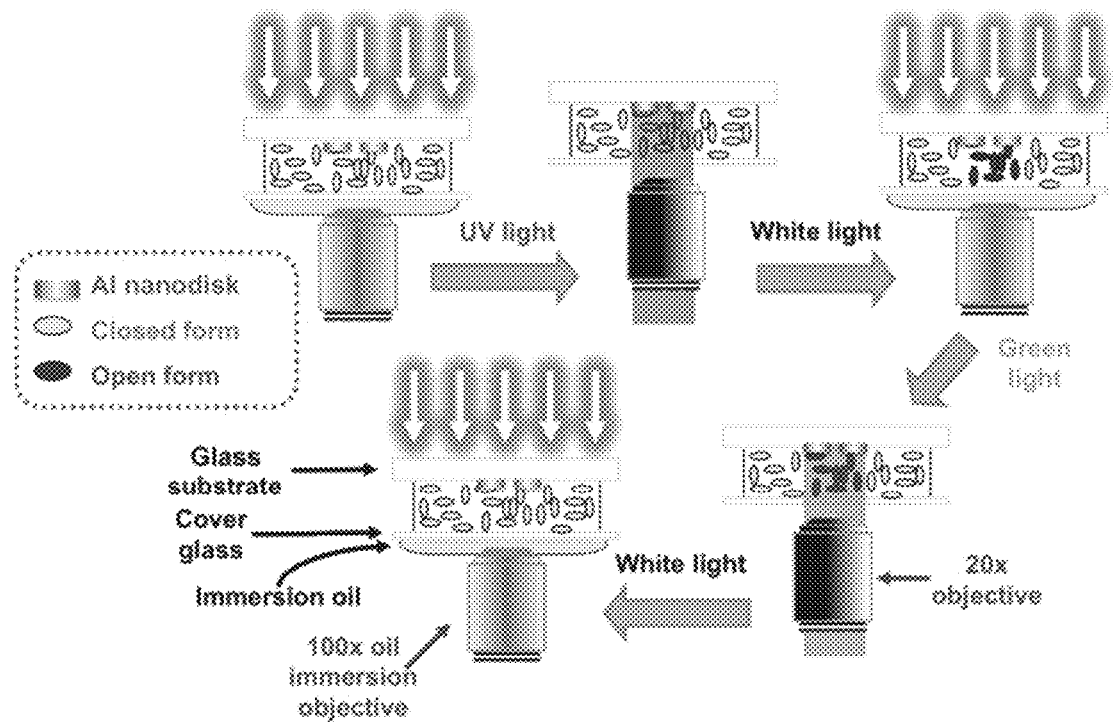
FIG. 14 is a schematic of a series of optical transmission measurements of the sample upon alternative irradiation of UV and green light. White light with transverse electric polarization was directed normally onto Al nanodisk arrays from the side of glass substrate. The transmission signals were collected by an oil-immersion objective (100×) and directed towards a spectrometer for analysis. UV and green light irradiated the sample through the 20× objective for 1 minute and 2 minutes, respectively, to switch the molecules.

A dark-field microscope (Ti-E inverted microscope, Nikon) with a halogen white light source (12V, 100 W) and an oil-immersion 100× objective were utilized to measure the transmission spectra of the samples. A linear polarizer (Thorlabs) was added between the light source and samples to generate the polarized light. A mercury light source (C-HGFIE, Nikon) with excitation filters was used to generate UV light (DAPI Shift Filter set, excitation wavelength: 325-375 nm) or green light (TRITC HYQ Shift Filter set, excitation wavelength: 530-560 nm) to switch molecules between their closed form (spiropyran) and open form (merocyanine). The schematic of the experimental procedure is shown in FIG. 14. All the transmission spectra were normalized with the background signal from the sample consisted of molecule (spiropyran or merocyanine)-doped PMMA thin film on glass substrate without Al nanodisk arrays.

A normal-incident white light with $E_x$ polarization was incident with the sample from the side of the glass substrate to interact with the Al nanodisk arrays, exciting both localized surface plasmon resonances and diffraction waves. The latter allows total internal reflection at the PMMA-substrate and PMMA-air interfaces to confine light within the PMMA waveguide layer. The coupling between light scattered from the Al nanodisks and light of transverse electric (TE) mode in the PMMA layer leads to the hybrid plasmon-waveguide modes (Zentgraf T et al. *Phys. Rev. B* 2009, 80, 195415; Rodriguez S R K et al. *Phys. Rev. Lett.* 2012, 109, 166803). The thickness of the PMMA waveguide layer was optimized using finite-difference time-domain (FDTD) simulations in order to tune the wavelengths of the hybrid plasmon-waveguide modes towards the absorption wavelength of the merocyanine molecules without introducing the higher-order waveguide modes.

FDTD simulations were performed using a commercial software (Lumerical Solutions). A linear-polarized plane-wave light source was incident with the sample normally from the side of the glass substrate and a detector was placed on the top of the sample to collect the transmission signal. Symmetric and asymmetric boundary conditions were applied in both ±x and ±y direction and perfect matching layers were applied in ±z direction. The refractive index of the glass substrate was set as 1.52, while the thickness and refractive index of the spiropyran molecule-doped PMMA was taken from the ellipsometry measurements. An ultra-fine mesh size (1 nm) was used in the simulations. The simulated transmission spectra with merocyanine molecules were normalized by the background signal from the structure of merocyanine molecule-doped PMMA thin film on glass substrate without Al nanodisk arrays.

Excited with a fluorescence light source, reversible photoisomerization of the molecules between their spiropyran form (irradiated with green light) and merocyanine form (irradiated with ultraviolet light) allows photoswitchable strong coupling between the molecular excitons and the hybrid plasmon-waveguide modes. The zero-order transmitted light, which was modulated with the photoswitchable Rabi splitting, was collected by an oil objective and directed towards a spectrometer for analysis.

Figure 15:
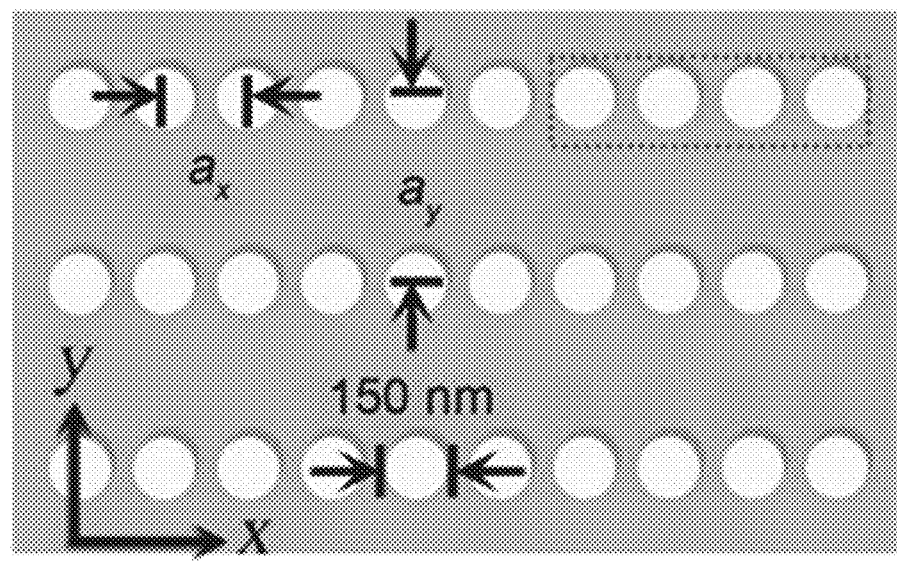
FIG. 15 is a top schematic view of the rectangular Al nanodisk array. The diameter of the Al nanodisks is 150 nm. The lattice constants were set to $a_x$=200 nm and $a_y$ ranging from 360 nm to 440 nm.
Figure 16:
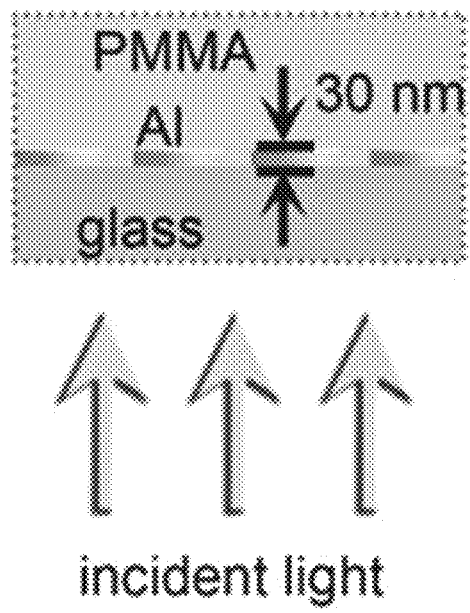
FIG. 16 is a cross-sectional schematic view of the Al nanodisk array. The height of Al nanodisks is 30 nm. The thickness of PMMA film is 280 nm.
Figure 17:
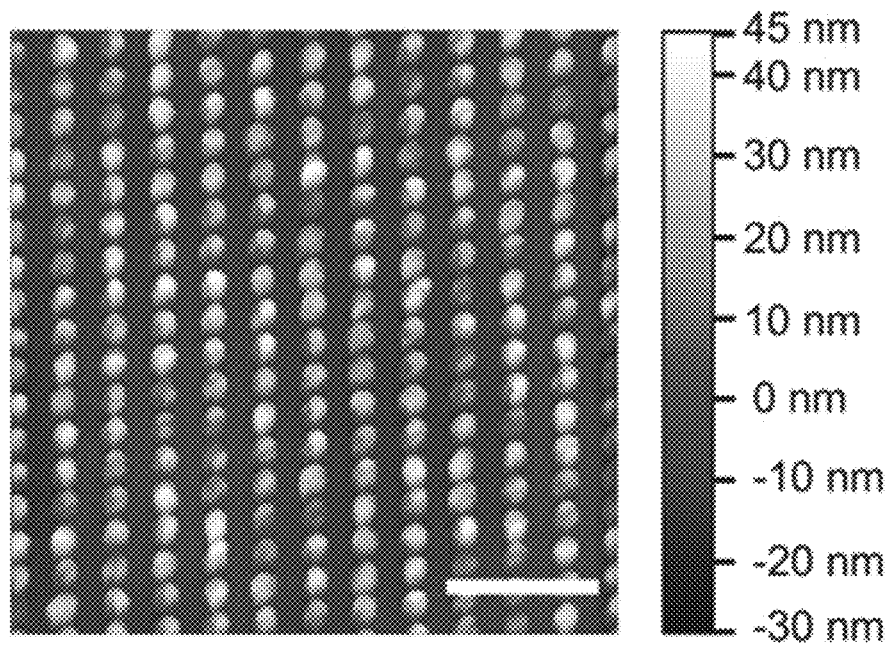
FIG. 17 is a 2D Atomic Force Microscopy (AFM) image of the Al nanodisk array with $a_y$=360 nm. Scale bar: 1 μm.
Figure 18:
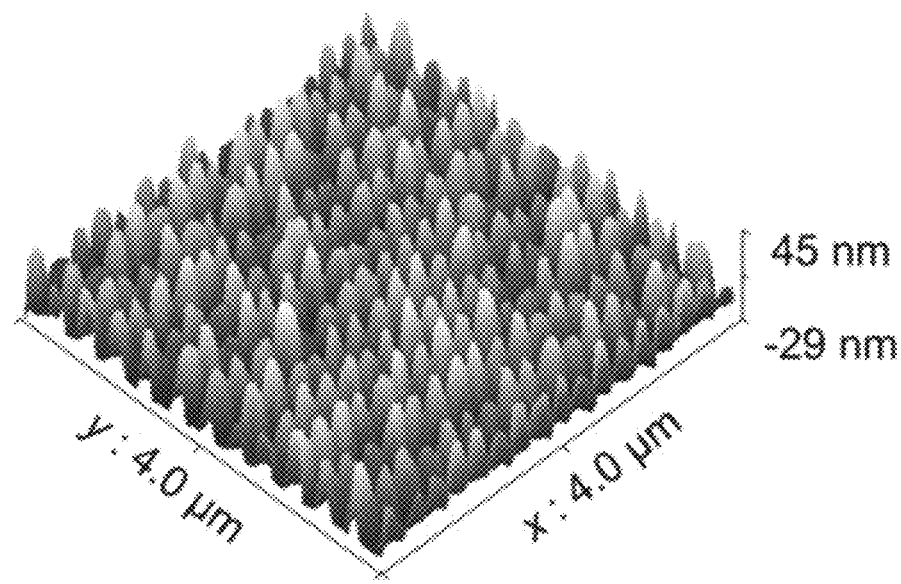
FIG. 18 is a 3D AFM image of the Al nanodisk array with $a_y$=360 nm.

FIG. 15 and FIG. 16 show planar and cross-sectional views, respectively, of the samples that support the hybrid plasmon-waveguide modes. The Al nanodisks had a diameter of 150 nm and a height of 30 nm. The lattice constant along the x-axis of the array ($a_x$) was set as 200 nm to introduce near-field coupling between adjacent Al nanodisks for the further enhancement of the localized electric field. The lattice constant along y-axis of the array ($a_y$) ranged from 360 nm to 440 nm to tune the resonant wavelength of the hybrid plasmon-waveguide modes in order to match the absorption wavelength of molecular excitons. Two-dimensional (2D) and three-dimensional (3D) atomic force micrographs (AFM) of representative Al nanodisk arrays fabricated with electron beam lithography (EBL) are displayed in FIG. 17 and FIG. 18, respectively.

Figure 19:
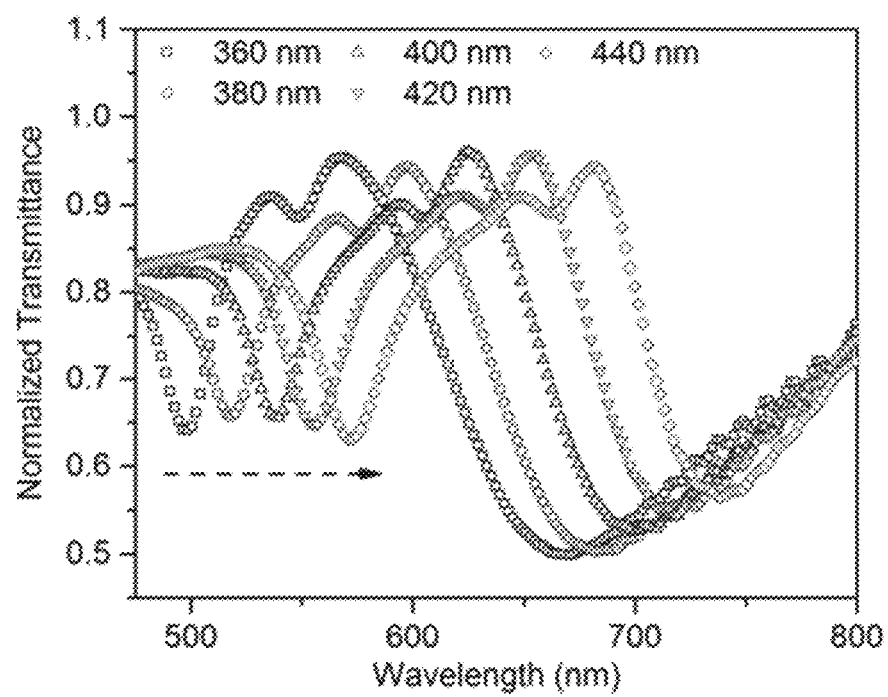
FIG. 19 is the normalized experimental transmission spectra of a series of samples with lattice constants $a_y$ from 360 to 440 nm.

To study the hybridization between localized surface plasmon resonances and waveguide modes in the samples, the transmission spectra was measured of the samples with variable lattice constants $a_y$ when photochromic molecules were in their spiropyran form. As shown in FIG. 19, the broad transmission dips from 670 nm to 750 nm, this dip originates from the intrinsic localized surface plasmon resonances of the Al nanodisks with near-field coupling. The dips in the transmission spectra at the shorter wavelengths (e.g., ~600 nm or less), which are narrower (and thus have a higher quality factor Q), arise from the hybrid plasmon-waveguide modes. The resonant wavelength of hybrid plasmon-waveguide modes can be tuned from 500 nm to 574 nm by changing the lattice constant $a_y$ (FIG. 19).

Figure 20:
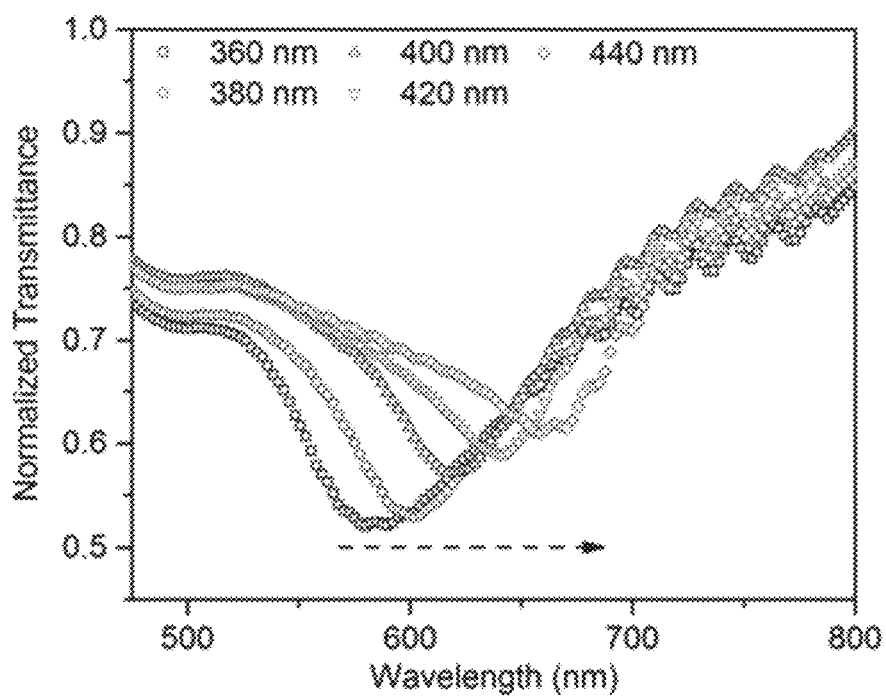
FIG. 20 is the experimental transmission spectra of bare Al nanodisk arrays with different lattice constants $a_y$.

For comparison, the transmission spectra of the bare Al nanodisk arrays on the glass substrate (e.g., without any PMMA coating) are shown in FIG. 20. The transmittance dips red shift from 570 nm to 660 nm as the lattice constant $a_y$ increases from 360 nm to 440 nm, indicating the coupling between the substrate diffraction orders of the arrays and the localized surface plasmon resonances from the Al nanodisks (Zentgraf T et al. *Phys. Rev. B* 2009, 80, 195415; Vecchi G et al. *Phys. Rev. Lett,* 2009, 102, 146807). The coupling is weak due to the cutoff of diffraction waves at the substrate-air interface.

By comparing the transmission spectra in FIG. 20 with those in FIG. 19, it can be seen that the localized surface plasmon resonance modes at the same lattice constants are located at the shorter wavelengths in FIG. 20 relative to those in FIG. 19 due to the lower refractive index of air than that of PMMA. In addition, the asymmetric surrounding environments (without the molecule-doped PMMA layer) weaken the far-field diffractive coupling between the Al nanodisks along y-axis.

Figure 21:
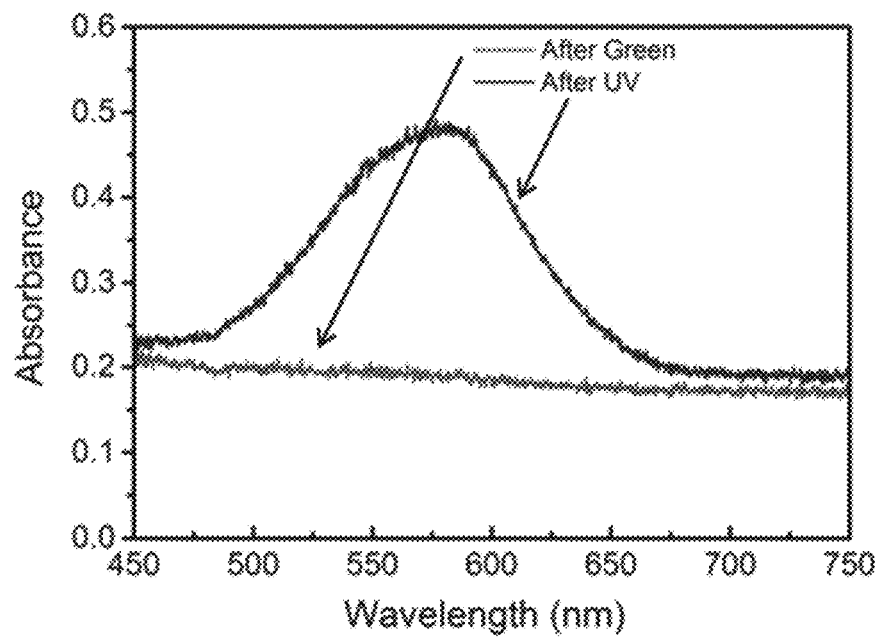
FIG. 21 is the experimental absorption spectra of merocyanine (After UV) and spiropyran molecules (After Green).

The absorption spectra in FIG. 21 show that the absorption peak wavelength of merocyanine molecules (After UV) is at 570 nm and the spiropyran molecules have no absorption of visible light. Comparing the absorption peak of the merocyanine molecules (FIG. 21) with the hybrid plasmon-waveguide modes of the samples (FIG. 19), it can be seen that there is a large spectral overlap between the hybrid plasmon-waveguide modes (FIG. 19) and molecular excitons (FIG. 21) to achieve the strong coupling.

Small dips between the intrinsic localized surface plasmon resonances and the hybrid plasmon-waveguide modes are seen in FIG. 19. These small dips arise from the diffraction orders at the Al nanodisk arrays. However, a robust coupling between the diffraction orders and the localized surface plasmon resonances does not exist because the thin layer of PMMA (280 nm) leads to an asymmetric refractive index of media surrounding the nanodisk arrays. Rather than generating lattice plasmon modes with narrow linewidth (e.g., tens of nanometers and below), the coupling is weak and leads to a slight redshift of the resonant wavelength and a slight narrowing of the linewidth of the localized surface plasmon resonances when the diffractive wavelength approaches the localized surface plasmon resonance wavelength. Due to the diffractive coupling, the broadened linewidth was bot observed in the localized surface plasmon resonances when the localized surface plasmon resonances approached the interband transition energy of Al (1.5 eV.~829 nm) (Chan G H et al. *J. Phys. Chem. C* 2008, 112, 13958-13963; Langhammer C et al. *Nano Let.* 2008, 8, 1461-1471).

Figure 22:
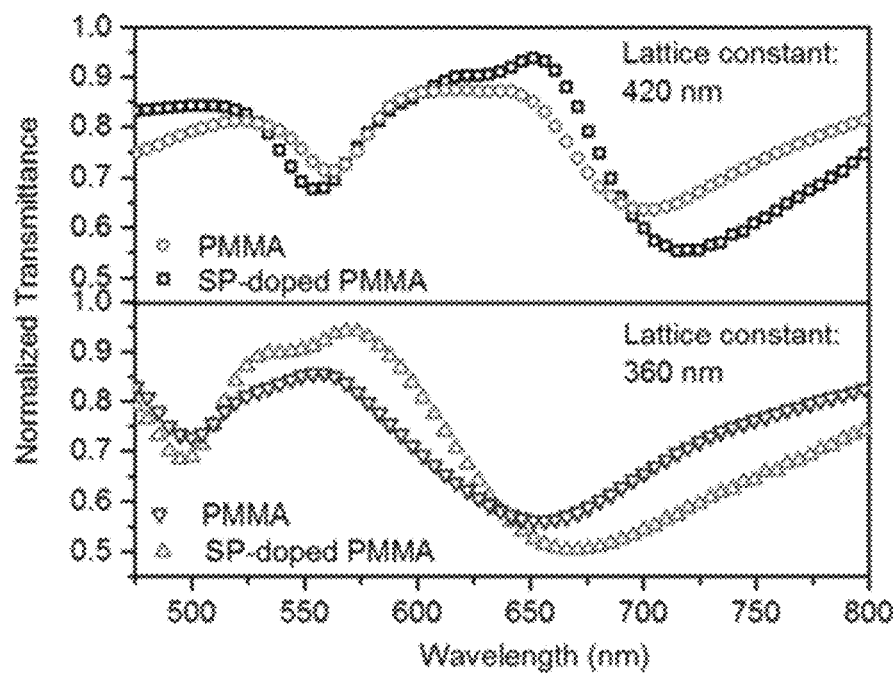
FIG. 22 shows a comparison of the experimental transmission spectra of PMMA coated Al nanodisk arrays with and without doping of spiropyran molecules at two different lattice constants: $a_y$=420 nm and $a_y$=360 nm.
Figure 23:
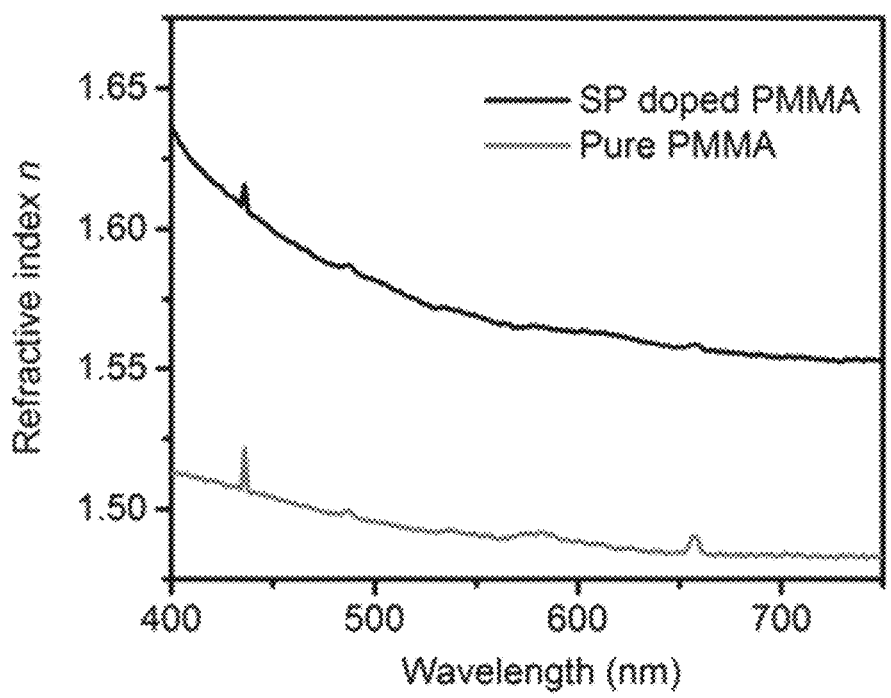
FIG. 23 is the measured refractive index of the PMMA layer with and without doping of spiropyran molecules.

In addition, the transmission spectra of PMMA-coated Al nanodisk arrays on glass substrates with and without doping of spiropyran molecules were investigated. In FIG. 22, the transmission spectra of PMMA coated Al nanodisk arrays with and without doping of spiropyran molecules at two different lattice constants, $a_y$=420 nm and $a_y$=360 nm, are shown. The localized surface plasmon resonances show a spectral redshift when the spiropyran molecules were doped in the PMMA layer, which is caused by the refractive index difference between the pure PMMA film and spiropyran molecules-doped PMMA film (FIG. 23). Based on the refractive-index change, a similar redshift in the transmission dips of the hybrid plasmon-waveguide modes was expected. However, a small blue shift is observed in FIG. 22. This blue shift can be attributed to the increased thickness of PMMA layer spin-coated on the substrate for the sample doped with the spiropyran molecules, as the hybrid plasmon-waveguide modes are known to be sensitive to the thickness of the PMMA layer.

The FDTD simulation results (FIG. 24) agree well with the experimental spectra. In the simulations, the dielectric function and thickness of the PMMA waveguide layer doped with spiropyran molecules were based on results from ellipsometry measurements. It is worth noting that, different from the hybrid waveguide-plasmon polaritons (HWPPs) near zero detuning (Christ A et al. *Phys. Rev. Lett.* 2003, 91, 183901; Zentgraf T et al. *Phys. Rev. B* 2009, 80, 195415; Rodriguez S R K et al. *Phys. Rev. Lett.* 2012, 109, 166803), the hybrid plasmon-waveguide modes were kept at large detuning in order to avoid the strong coupling between the waveguide modes and the localized surface plasmon resonances, which can cause the splitting of the hybrid modes and electromagnetically induced transparency (EIT) at the resonant wavelength (Oulton R F et al. *Nat Photon* 2008, 2, 496-500; Rodriguez S R K et al. *Phys. Rev. Lett.* 2012, 109, 166803).

Figure 25:
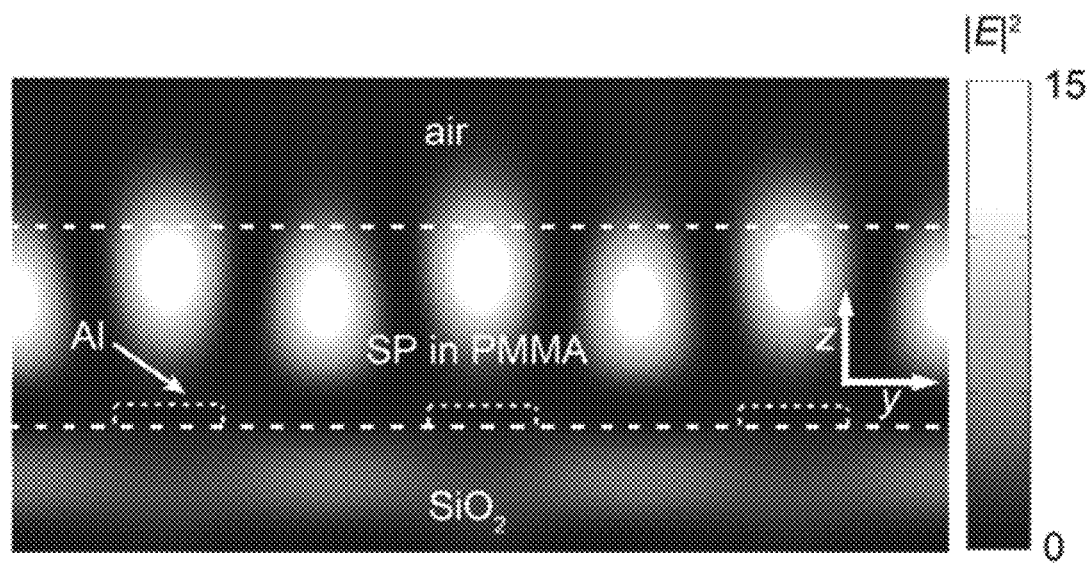
FIG. 25 is the simulated electromagnetic field intensity distribution for a sample with the lattice constant $a_y$=440 nm at λ=574 nm in the yz plane.
Figure 26:
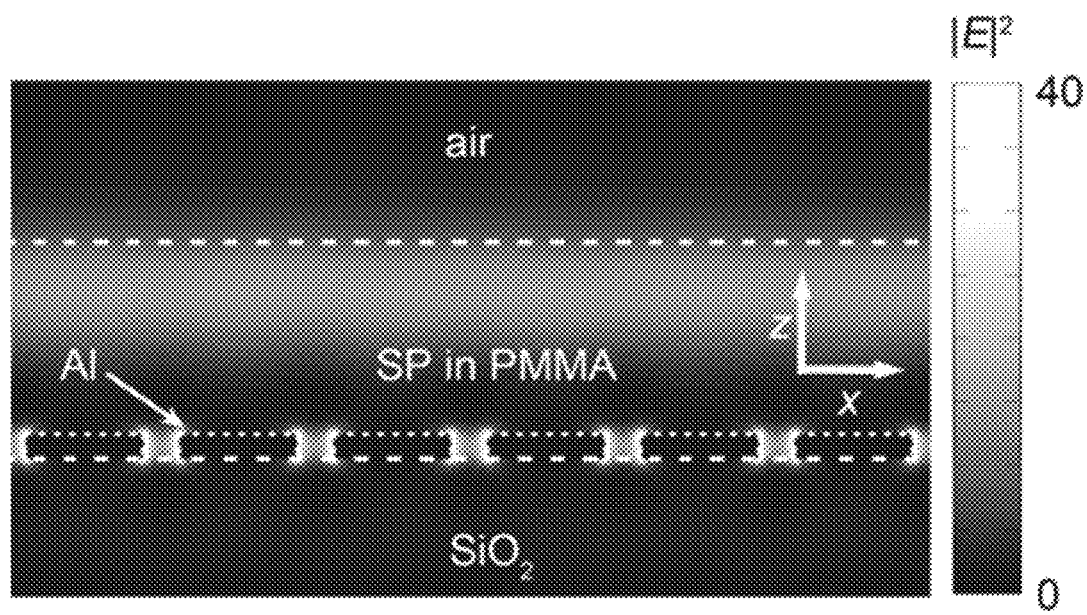
FIG. 26 is the simulated electromagnetic field intensity distribution for a sample with the lattice constant $a_y$=440 nm at λ=574 nm in the xz plane.
Figure 27:
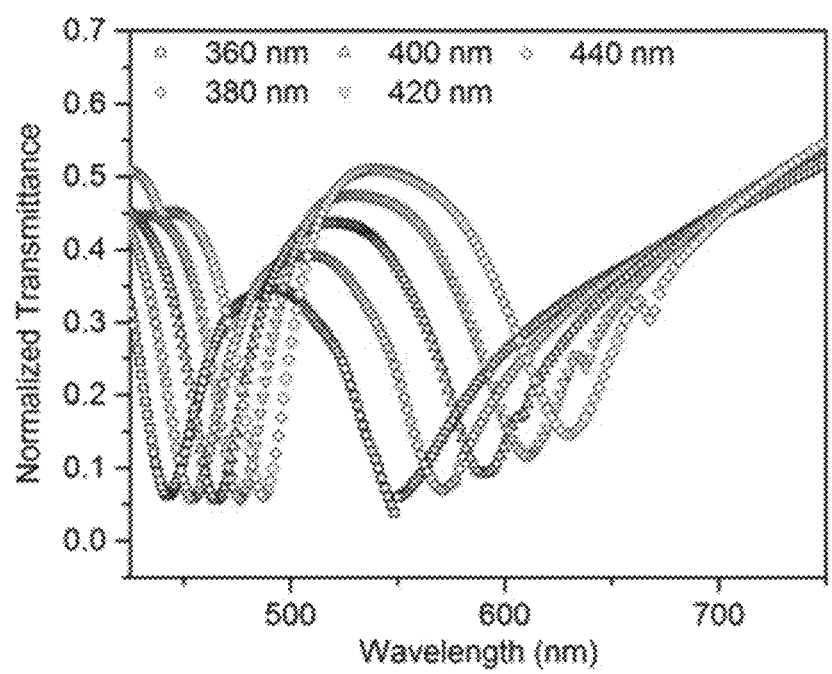
FIG. 27 is the simulated transmission spectra of Al nanodisk arrays with variable lattice constants $a_y$ with the incident light of transverse magnetic polarization (along y-axis).
Figure 28:
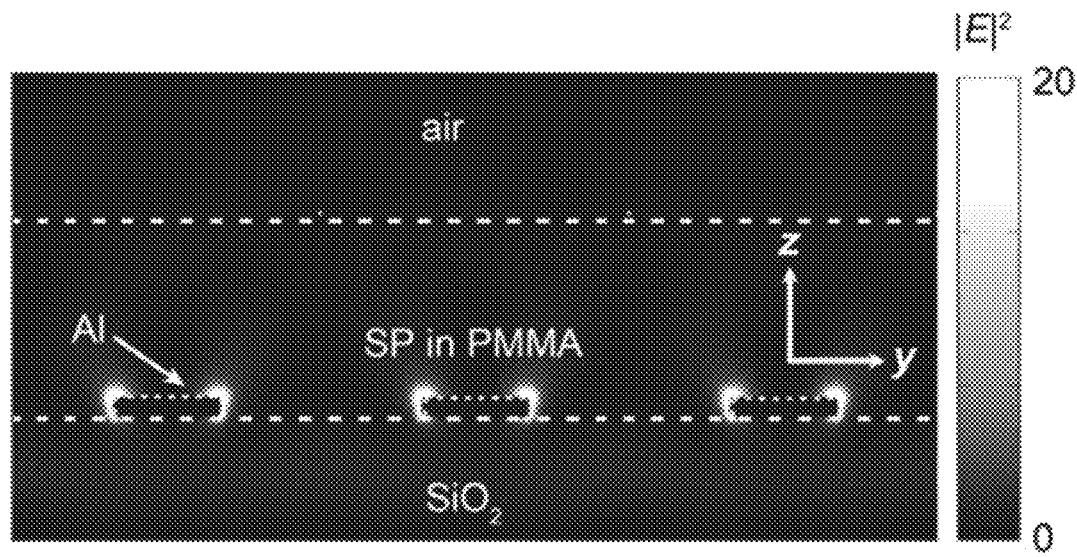
FIG. 28 is a cross-sectional view of the simulated distribution of electric field intensity at the wavelength of 630 nm (transverse magnetic polarization) for the Al nanodisk array with $a_y$=440 nm.

To better understand the nature of the hybrid plasmon-waveguide modes, the electric field distributions for different modes revealed by the transmission spectrum of the sample with $a_y$=440 nm were simulated. As shown in FIG. 25, at the resonant wavelength of the hybrid plasmon-waveguide mode ($\lambda$=574 nm), a transverse electric propagating waveguide mode (x-polarized and propagating along y-axis) is observed in the yz plane. This can be attributed to constructive interference between total reflection light at the PMMA-air interface and diffraction waves from the periodic Al nanodisk arrays. For the same wavelength ($\lambda$=574 nm), the localized surface plasmon resonance-like dipole mode with near-field coupling between adjacent nanodisks is excited along x direction in the xz plane, as shown in FIG. 26. For comparison. FIG. 27 shows the optical spectra and FIG. 28 shows the electric field distribution under the excitation of transverse magnetic (TM)-polarized light. The localized surface plasmon resonance-like mode in the hybrid plasmon-waveguide modes can originate from the multiple interactions between the propagating light in the waveguide layer and the Al nanodisk arrays, which can cause collective coupling between the individual Al nanodisks and improve the electric field intensity of the plasmonic dipoles.

Figure 29:
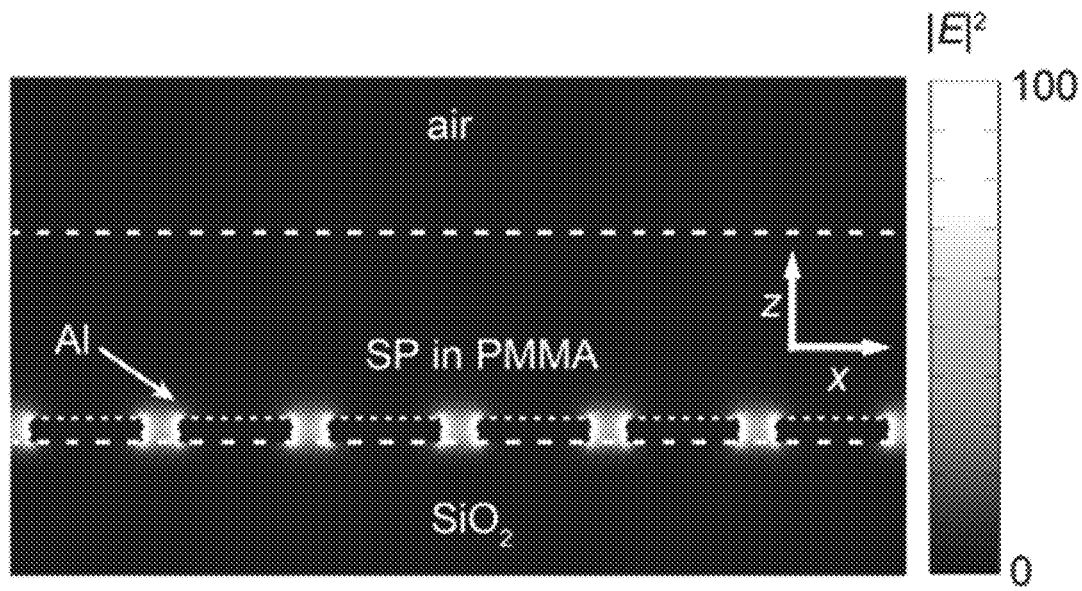
FIG. 29 is the simulated electromagnetic field intensity distribution for a sample with the lattice constant $a_y$=440 nm at λ=800 nm in the xz plane.
Figure 30:
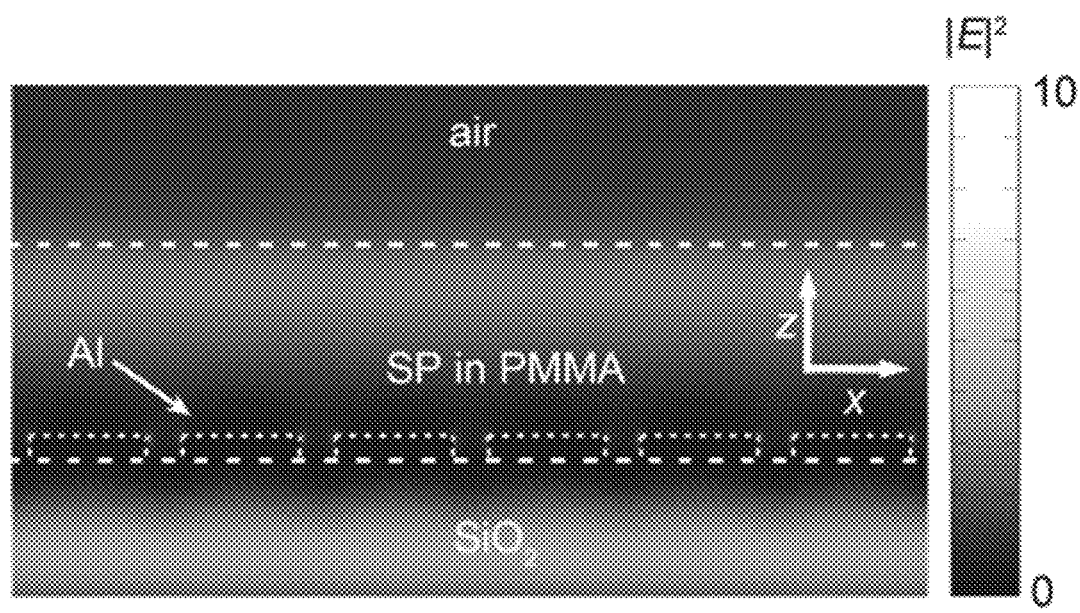
FIG. 30 is the simulated electromagnetic field intensity distribution for a sample with the lattice constant $a_y$=440 nm at λ=625 nm in the xz plane.

Although the resonant wavelength of the hybrid plasmon-waveguide mode, $\lambda$=574 nm, is far away from the resonant wavelength of the localized surface plasmon resonances, $\lambda$=800 nm (i.e., there is a large detuning), the hybrid plasmon-waveguide modes exhibit features of the localized surface plasmon resonances, which is different from the bare waveguide mode. For comparison, the electric field distribution of the localized surface plasmon resonance mode at 800 nm is displayed in FIG. 29. This electric field distribution reveals a bare dipolar localized surface plasmon resonance mode without any signatures of propagating waveguide. Moreover, the electric field distribution at $\lambda$=625 nm which is closer to the localized surface plasmon resonance at 800 nm but not on resonance with hybrid plasmon-waveguide mode, reveals that the sample is transparent to this incident light without an observation of plasmonic dipole mode (FIG. 30). Thus, the plasmonic dipole observed in the hybrid plasmon-waveguide mode ($\lambda$=574 nm) does not originate from the intrinsic localized surface plasmon resonances around 800 nm. The hybridization between the localized surface plasmon resonances and the waveguide mode significantly reduce the full-width at half-maximum (FWHM) of the hybrid plasmon-waveguide modes, which ranges from 106 meV to 132 meV according to the transmission spectra in FIG. 19. In contrast, the bare localized surface plasmon resonance modes at the longer wavelength show the much broader linewidth (FIG. 19); for example, the full-width at half-maximum is 520 meV for the sample with $a_y$=360 nm.

To demonstrate the strong coupling between the excitons of merocyanine molecules and the hybrid plasmon-waveguide modes, the samples were irradiated with UV light and the transmission spectra were then measured. Upon UV irradiation, the photochromic molecules isomerized from the spiropyran form to the merocyanine form, and the merocyanine form features an absorption peak at a wavelength of 570 nm (FIG. 21). The spectral overlap between the hybrid plasmon-waveguide modes and merocyanine molecules leads to strong coupling between them and the Rabi splitting occurs (Hutchison J A et al. *Adv. Mater.* 2013, 25, 2481-

2485; Hutchison J A et al. *Angew. Chem. Int. Ed.* 2012, 51, 1592-1596; Schwartz T et al. *Phys. Rev. Lett.* 2011, 106, 196405).

Figure 24:
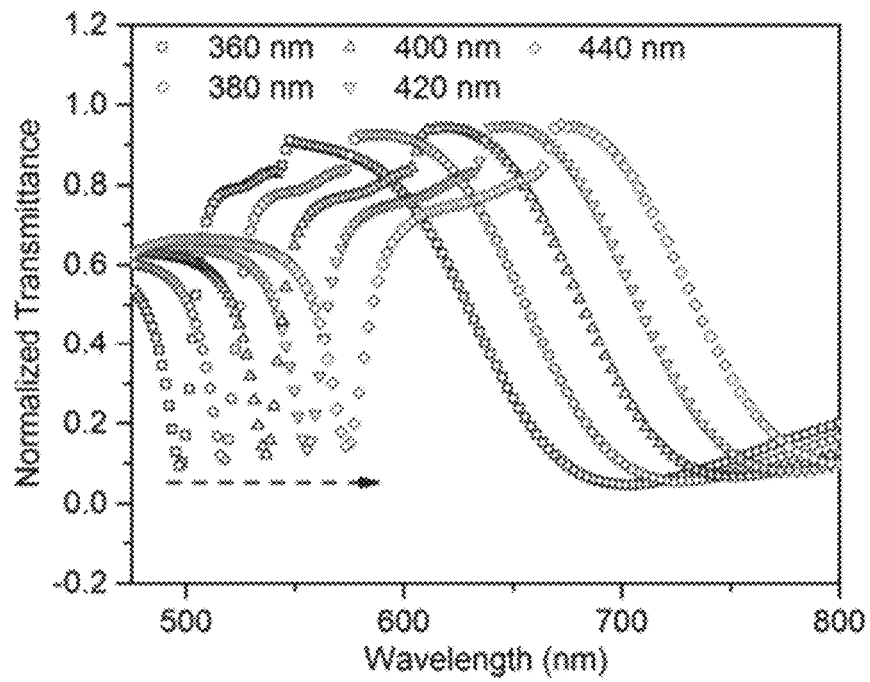
FIG. 24 is the normalized simulated transmission spectra of a series of samples with the lattice constants $a_y$ from 360 to 440 nm.

The intrinsic localized surface plasmon resonances blue shift when the incident light changes from transverse electric to transverse magnetic polarization (FIG. 24 and FIG. 27). The blue shift verifies that there is near-field coupling between neighboring Al nanodisks at the excitation with light of transverse electric polarization (i.e., along x-axis). However, no such near-field coupling occurs when the incident light is transverse magnetic-polarized due to the increased inter-disk distance along this polarization direction (i.e., along y-axis). The blue shift of the localized surface plasmon resonances also blue shifts the hybrid plasmon-waveguide modes (FIG. 27), which prevents the spectral overlap between the hybrid plasmon-waveguide modes and the optical absorption of merocyanine molecules for transverse magnetic polarization.

Figure 31:
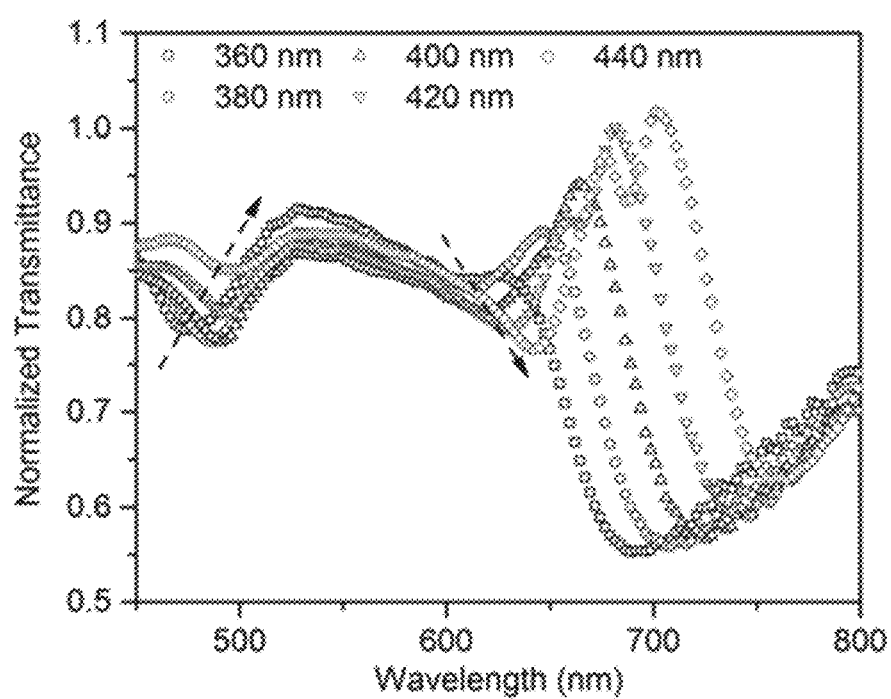
FIG. 31 is the normalized experimental transmission spectra of a series of samples after UV light irradiation. The black arrows indicate the shifts in dip wavelengths upon an increase of the lattice constant $a_y$.
Figure 32:
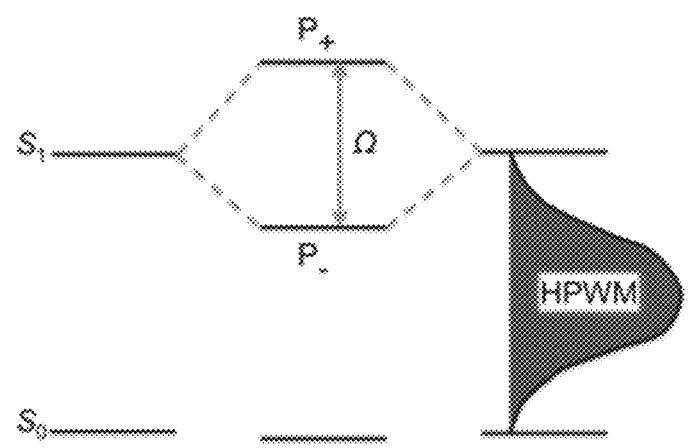
FIG. 32 is a schematic of strong coupling between merocyanine molecules and the hybrid plasmon-waveguide mode, which leads to Rabi splitting. $S_0$ and $S_1$ are ground state and first excited state of merocyanine molecules, respectively. Two new polaritonic states ($P_+$ and $P_-$) are formed with separation of Rabi splitting energy (Ω).

As shown in FIG. 31, the single transmission dips of the hybrid plasmon-waveguide modes have developed into two dips upon conversion of the spiropyran to merocyanine, with the maximum Rabi splitting energy of 572 meV at $a_y$=430 nm. A redshift of the localized surface plasmon resonances was also observed when the spiropyran molecules were switched to the merocyanine form (compare FIG. 19 and FIG. 31), which is caused by the photoisomerization-induced refractive index change in the molecules (Zheng Y B et al. *Nano Lett.* 2011, 11, 2061-2065). The energy transfer between the hybrid plasmon-waveguide modes and merocyanine molecules upon strong coupling creates two new polaritonic states: upper polaritonic state ($P_+$) and lower polaritonic state ($P_-$) (FIG. 32), which are separated by the Rabi splitting energy $\Omega$ as defined below (Törmä P and Barnes W L. *Rep. Prog. Phys.* 2015, 78, 013901):

$$\Omega = \sqrt{\frac{N}{V} \frac{f_0 e^2}{\varepsilon_0 m}} \quad (1)$$

where N is the number of coupled molecules in the system, V is the effective mode volume, $f_0$ is the oscillator strength of molecules, $\varepsilon_0$ is the vacuum permittivity, e is the electron charge, and m is the electron mass. To further confirm that Rabi splitting is responsible for the observed spectral evolution, it was shown that the criterion of Rabi splitting is satisfied herein: $\Omega > (\gamma_{HPWM} + \gamma_0)/2$ (Khitrova G et al. *Nat Phys* 2006, 2, 81-90; Savasta S et al. *ACS Nano* 2010, 4, 6369-6376) where $\gamma_{HPWM}$=141 meV is full-width at half-maximum of the hybrid plasmon-waveguide modes, and $\gamma_0$=497 meV is full-width at half-maximum of the absorption band of merocyanine molecules. For the largest splitting energy, $\Omega$=572 meV>$(\gamma_{HPWM}+\gamma_0)/2$=319 meV.

Figure 33:
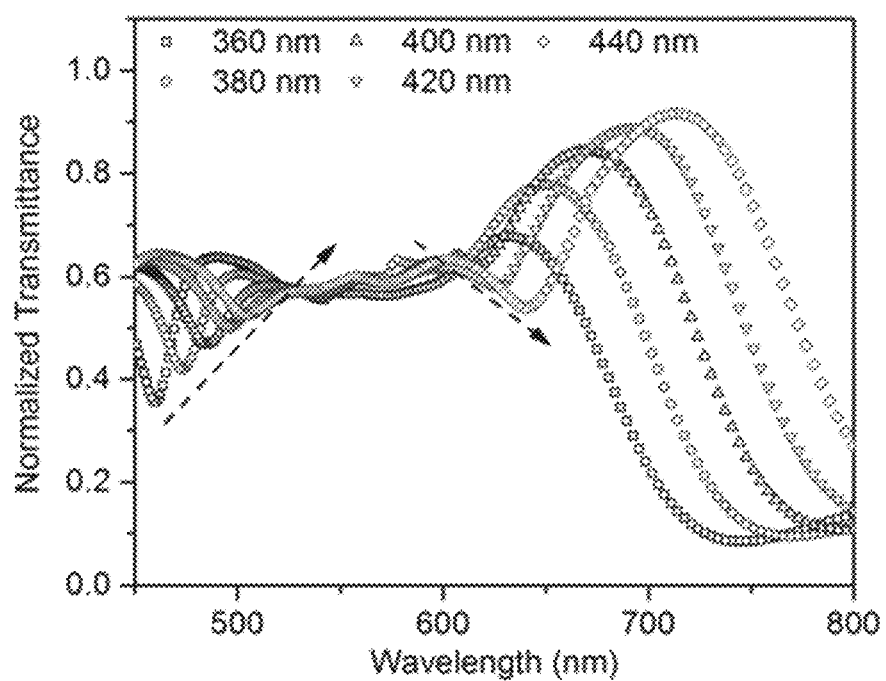
FIG. 33 is the normalized simulated transmission spectra of a series of samples after UV light irradiation. The black arrows indicate the shifts in dip wavelengths upon an increase of the lattice constant $a_y$.
Figure 34:
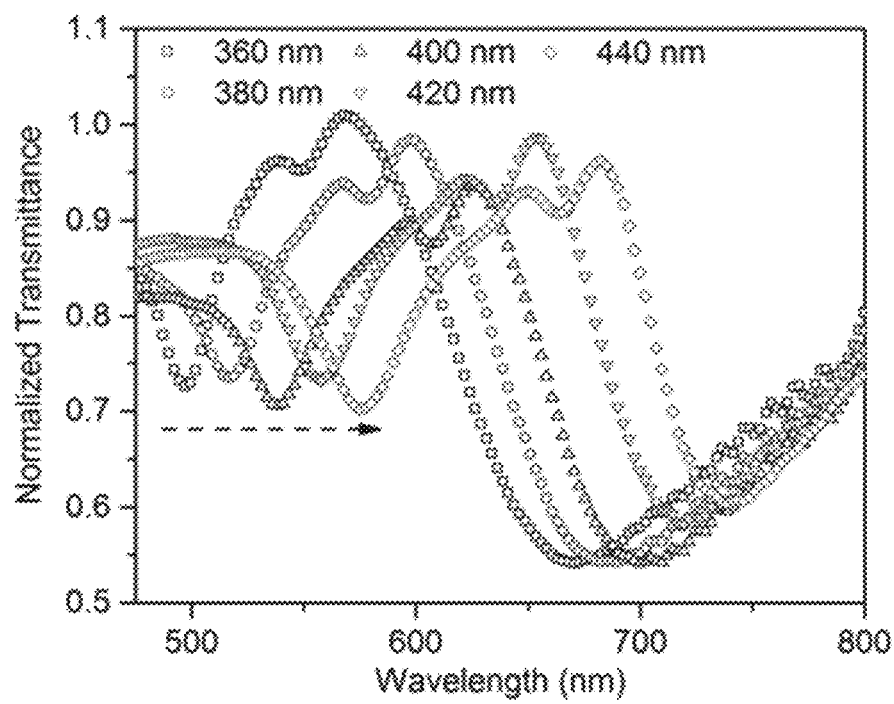
FIG. 34 is the normalized experimental transmission spectra of the same series of samples as in FIG. 31 after green light irradiation. The black arrows indicate the shifts in dip wavelengths upon an increase of the lattice constant $a_y$.
Figure 35:
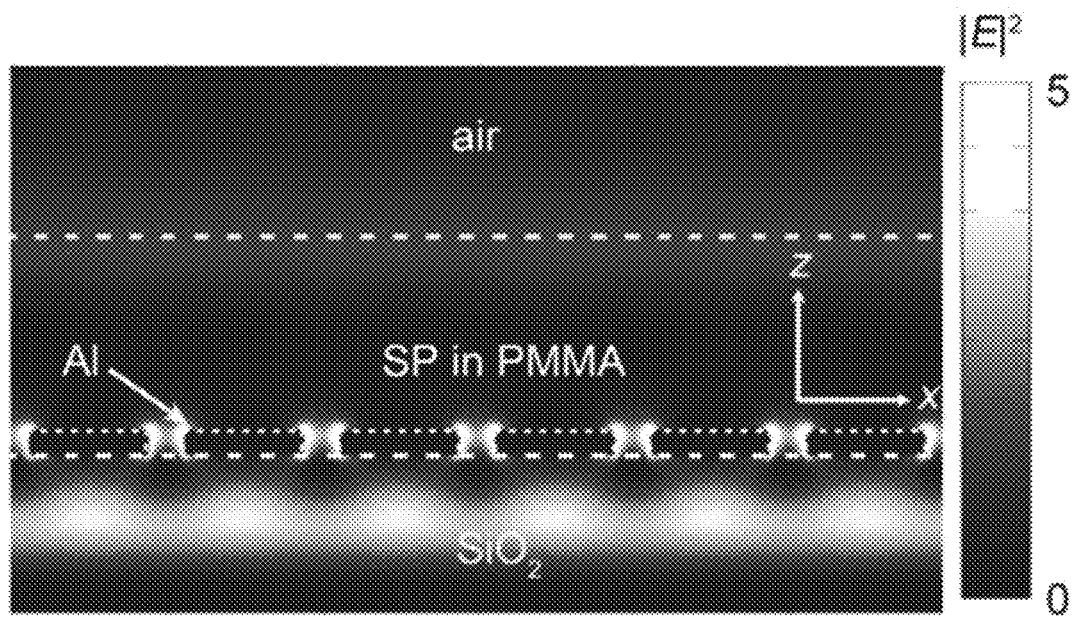
FIG. 35 is the electric field distribution of the hybrid plasmon-waveguide modes after Rabi splitting with the lattice constant $a_y$=440 nm at λ=504 nm in the xz plane.
Figure 36:
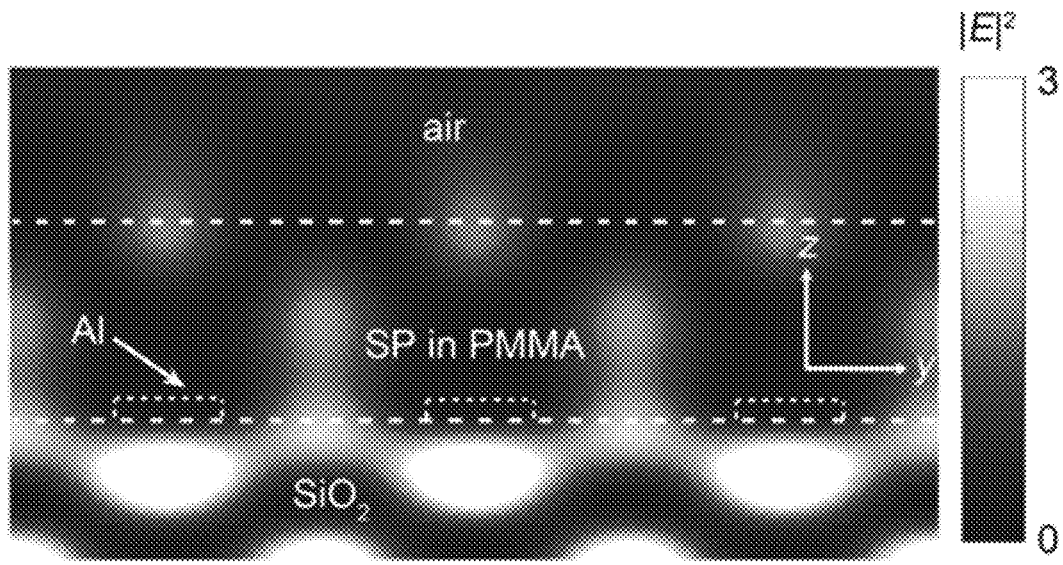
FIG. 36 is the electric field distribution of the hybrid plasmon-waveguide modes after Rabi splitting with the lattice constant $a_y$=440 nm at λ=504 nm in the yz plane.
Figure 37:
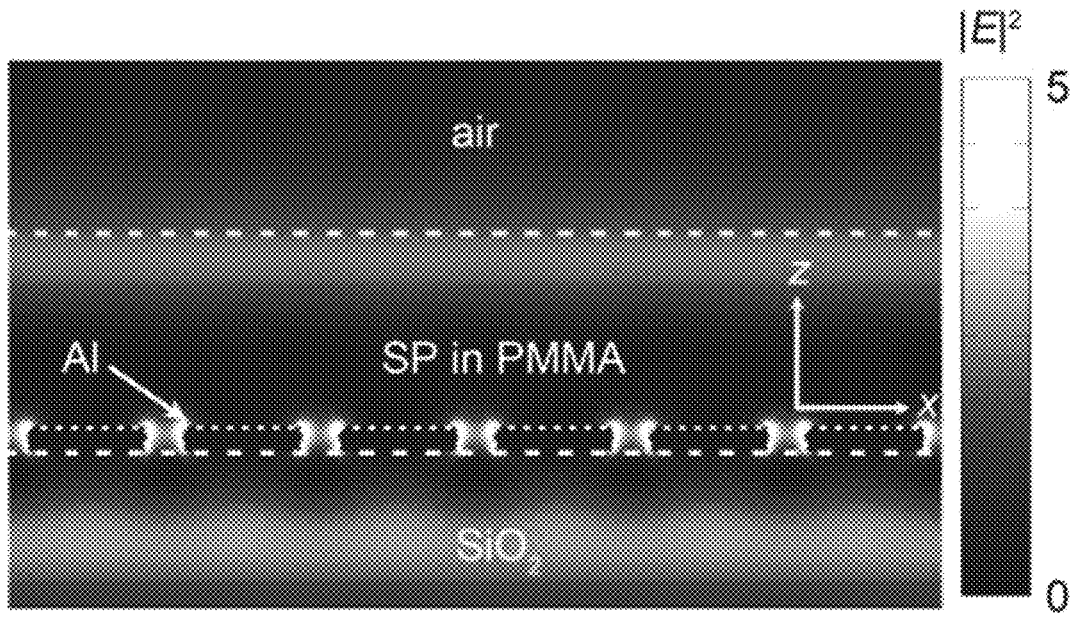
FIG. 37 is the electric field distribution of the hybrid plasmon-waveguide modes after Rabi splitting with the lattice constant $a_y$=440 nm at λ=640 nm in the xz plane.
Figure 38:
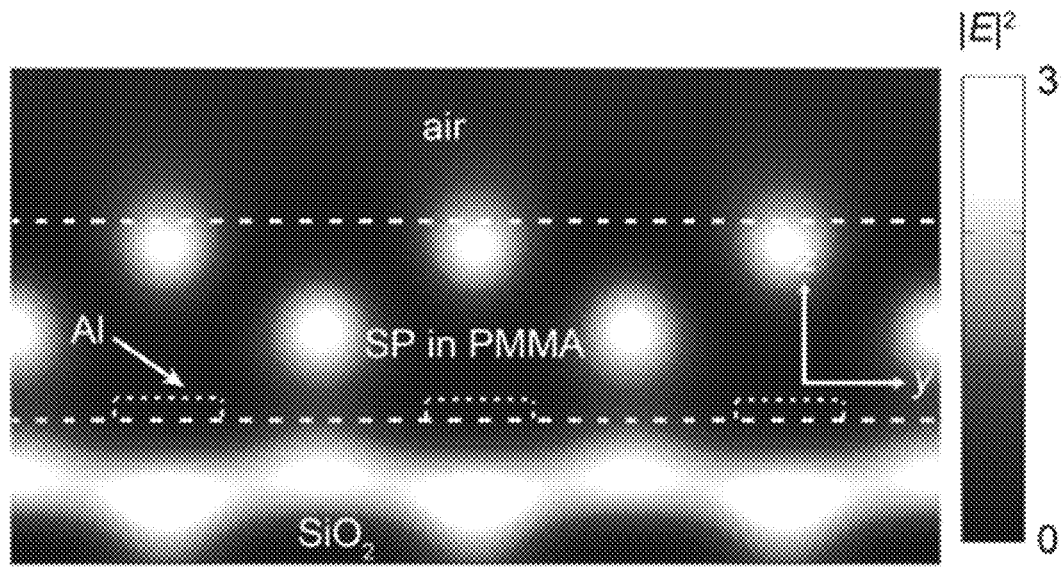
FIG. 38 is the electric field distribution of the hybrid plasmon-waveguide modes after Rabi splitting with the lattice constant $a_y$=440 nm at λ=640 nm in the yz plane.

The transmission spectra of the series of samples were simulated at the strong coupling between the hybrid plasmon-waveguide modes and merocyanine molecules, with the frequency-dependent permittivity of merocyanine molecules treated as a dimensionless Lorentz oscillator (Eizner E et al. *Nano Lett.* 2015, 15, 6215-6221; Zengin G et al. *Sci. Rep.* 2013, 3, 3074):

$$\varepsilon(\omega) = \varepsilon_\infty + \frac{f\omega_X^2}{\omega_X^2 - \omega^2 - i\gamma\omega} \quad (2)$$

where $\varepsilon_\infty$=2.46 is the bound electron permittivity taken from the ellipsometry results for spiropyran molecules, $\omega_X$=3.35×$10^{15}$ rad/s is the oscillator frequency of the molecules as calculated from the absorption wavelength, $\gamma$=2×$10^{14}$ rad/s is the damping constant determined from the linewidth of the absorption band, and f=0.17 is the oscillator strength. The simulated transmission spectra (FIG. 33) agree well with the experimental spectra (FIG. 31). Further, the experimental transmission spectra of the series of samples shown in FIG. 31 were collected after irradiation with green light, which switches the merocyanine back to spiropyran and are shown in FIG. 34.

FIG. 35-FIG. 38 show the distributions of electric field intensity of the hybrid plasmon-waveguide mode after being strongly coupled with the merocyanine molecules for the sample with $a_y$=440 nm. Further examination of the electric field profiles at the two transmission dip wavelengths, $\lambda$=504 nm and $\lambda$=640 nm, reveals that two separated hybrid plasmon-waveguide modes exist at these two wavelengths, confirming the occurrence of Rabi splitting of hybrid plasmon-waveguide modes upon coupling with the merocyanine molecules (FIG. 35-FIG. 38). After the Rabi splitting, the intensities of the electric fields become lower due to the loss induced by the absorption of merocyanine molecules.

Besides the large oscillator strength of merocyanine molecules at room temperature (Törmä P and Barnes W L. *Rep. Prog. Phys.* 2015, 78, 013901; Schwartz T et al. *Phys. Rev. Lett.* 2011, 106, 196405), which determines the permittivity change around the oscillator frequency (Eq. 2), an improved quality factor Q of the hybrid plasmon-waveguide modes strengthens their strong coupling with the molecular exciton and thus leads to a large Rabi splitting observed herein. The quality factor Q is defined as (Sonnichsen C et al. *Phys. Rev. Lett.* 2002, 88, 077402):

$$Q = \frac{E_r}{\gamma}$$

where $E_r$ and $\gamma$ are the resonant energy and the full-width at half-maximum (FWHM) of the optical mode, respectively. The hybrid plasmon-waveguide modes ($a_x$=360 nm) have a Q factor of 23.6, compared with a Q factor of 2.4 for the localized surface plasmon resonances of the bare Al nanodisk array with the same lattice constant (FIG. 20). Therefore, a dramatic improvement of Q factor was gained by the hybridization between localized surface plasmon resonance modes and waveguide modes. Since $$\frac{\Omega}{2\gamma_P} \sim Q\sqrt{N/V}$$

(Zengin G et al. *Phys. Rev. Lett.* 2015, 114, 157401), assuming that the ratio of coupled molecules to uncoupled molecules is constant among the total mode volume of the hybrid plasmon-waveguide modes, a large quality factor Q (23.6 when $a_x$=360 nm) and a larger plasmon damping $\gamma_p$ (defined as v/Q, where v is the frequency of hybrid plasmon-waveguide modes) (Zengin G et al. *Phys. Rev. Lett.* 2015, 114, 157401) lead to a larger coupling strength.

Figure 39:
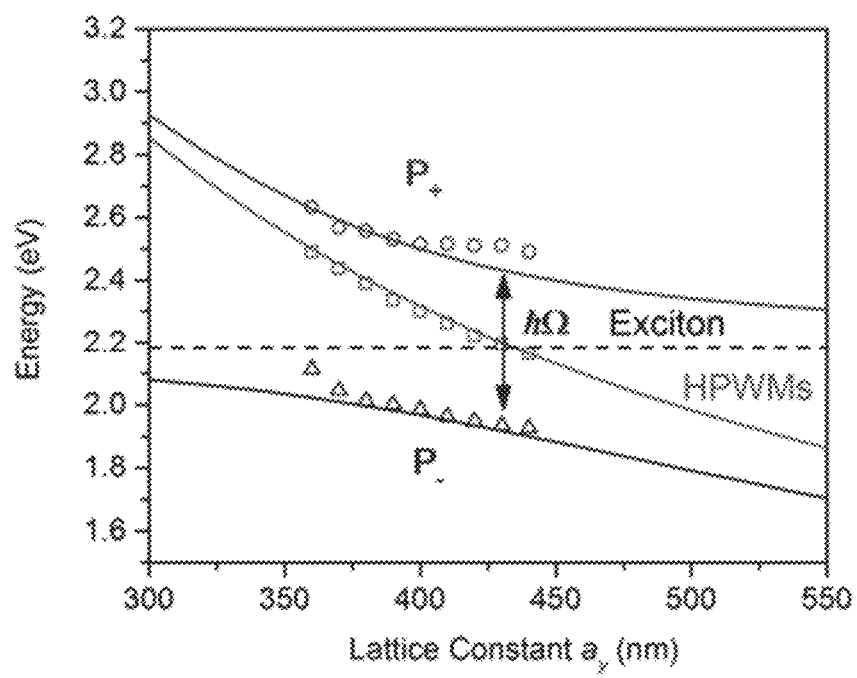
FIG. 39 is the energies of hybrid plasmon-waveguide modes (squares) experiences an anticrossing near the exciton energy of merocyanine molecules (dashed horizontal line) due to the strong coupling. Circles and triangles indicate the energies of $P_+$ state and $P_-$ state, respectively, as a function of lattice constant $a_y$ (as shown in FIG. 15). The dispersive dip branches of $P_+$ and $P_-$ states are fitted using the two-coupled-oscillators model. The energies of the hybrid plasmon-waveguide modes were extended using simulation data. Largest photoswitchable Rabi splitting occurs to the sample with $a_y$=430 nm.

Another signature of the strong coupling between the hybrid plasmon-waveguide modes and merocyanine molecular excitons and Rabi splitting is the energy anti-crossing (Törmä P and Barnes W L. *Rep. Prog. Phys.* 2015, 78, 013901). The energies of the hybrid plasmon-waveguide modes before and after UV light illumination and the absorption energy of the merocyanine molecules are summarized in FIG. 39. The dispersions were fitted using the two-coupled-oscillators model. When the energies of hybrid plasmon-waveguide modes are tuned (by changing the lattice constant $a_y$ of the Al nanodisk arrays) across the exciton energy of merocyanine molecules (i.e., 2.18 eV, as indicated by dashed horizontal line), two dispersive dip branches, the upper and lower polaritons $P_+$ and $P_-$, undergo an anticrossing at the exciton energy. Since all the data points are close to the zero-detuning point, the energy differences among these lattice constants are small.

One example application of the photoswitchable Rabi splitting in the hybrid plasmon-waveguide modes is all-optical modulation. As displayed in FIG. 40, the transmission spectrum for the as-prepared sample features a dip at the wavelength of 560 nm (the resonance wavelength of the hybrid plasmon-waveguide mode with $a_y$=430 nm). This dip develops into two dips with wavelengths shifted to 500 nm and 640 nm after UV light irradiation of the sample (FIG. 40), which isomerizes the molecules to merocyanine form and leads to the Rabi splitting. The single dip at the wavelength of 560 nm is restored after green light irradiation (FIG. 40), which isomerizes the merocyanine molecules back to the spiropyran form and the Rabi splitting disappears. Thus, one can devise all-optical modulators based on this photoswitchable Rabi splitting (Baudrion A L et al. *Nano Lett.* 2013, 13, 282-286).

The hybrid systems described herein can support the photoswitchable Rabi splitting in the hybrid plasmon-waveguide modes, which enables optical tuning of the resonant wavelengths of hybrid plasmon-waveguide modes. The photoswitchable resonant wavelengths of the hybrid plasmon-waveguide modes could be harnessed for optically rewritable waveguides.

To investigate the ability of the hybrid systems describes herein to be used as optically rewritable waveguides, a UV lamp was used to switch spiropyran molecules to their merocyanine form in the whole samples before the optical writing. A 532 nm laser beam (Coherent, the maximum power is 1.1 W) was employed to write the waveguides on the Al nanodisk arrays covered with the merocyanine-doped PMMA film. A half-wave plate was employed to control the polarization of the laser beam. A 5× beam expander was used to expand the laser beam. A digital micromirror device (DMD) was integrated into the optical setup to scan the laser beam with controllable power, size and speed. A square-patterned laser beam was generated by the digital micromirror device and focused onto the samples. The size of the beam was reduced by 500 times after being relayed by a 1000 mm doublet lens, a 200 mm doublet lens, an infinity-corrected tube lens and a 100× objective (NA=0.9). Either the digital micromirror device or motorized stage in the optical microscope was utilized to scan the laser beam on the samples for the writing process. Optical images and videos were recorded with a color digital microscope camera (Nikon).

Figure 40:
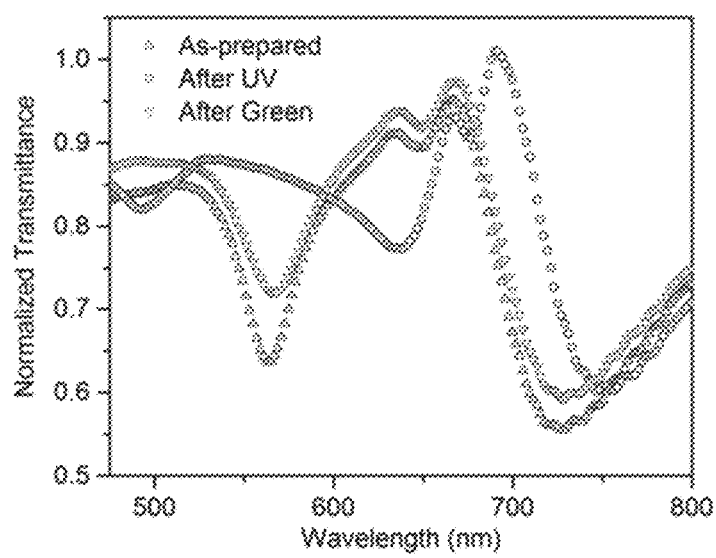
FIG. 40 is the transmission spectra for as-prepared (Δ) sample with $a_y$=430 nm, after UV irradiation (o), and after irradiation with green light (∇).
Figure 41:
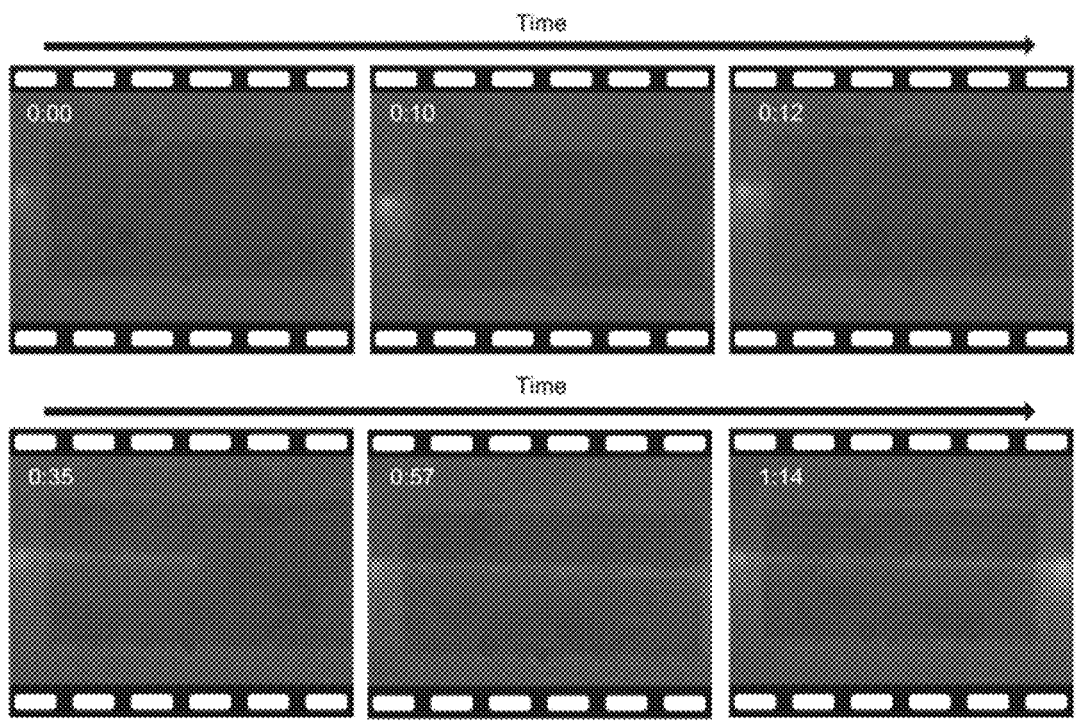
FIG. 41 is successive optical images of the optical writing of a waveguide (as a straight line) on the merocyanine-molecule-doped PMMA on Al nanodisk array. The writing process was completed within 1 min. The dark rectangular regime corresponds to the Al nanodisk array. Both digital micromirror device and motorized stage were applied to control a green laser beam for the waveguide writing. Upon green laser irradiation, the photochromic molecules were switched from merocyanine to spiropyran form.

Real-time writing of a waveguide on the Al nanodisk array ($a_y$=430 nm) covered with merocyanine-molecule-doped PMMA film was demonstrated, as displayed in the successive optical images in FIG. 41. A green laser beam (532 nm) generated with the digital micromirror device was focused on the sample through a 100× objective. The digital micromirror device and motorized stage-controlled scanning of the laser beam from one side of the Al nanodisk array along y axis created a channel, where the merocyanine molecules were switched to their spiropyran form. The bright color on the exposed region suggests that the sample becomes more transparent due to the weak absorption of visible light by the spiropyran molecules (FIG. 21). At t=1:14, a waveguide with a width of about 2 μm (the straight line) is written on the sample (FIG. 41). This waveguide can support hybrid plasmon-waveguide mode at the peak wavelength of 560 nm according to the optical spectrum in FIG. 40, while the unexposed areas with merocyanine form can support hybrid plasmon-waveguide modes at the wavelengths of 500 nm and 640 nm (FIG. 40). Thus, light with a wavelength of 560 nm can be guided along the straight line, leading to the optical creation of a waveguide. In principle, with the digital micromirror device-based control of the writing laser beam, waveguides with arbitrary designs can be created optically.

Figure 42:
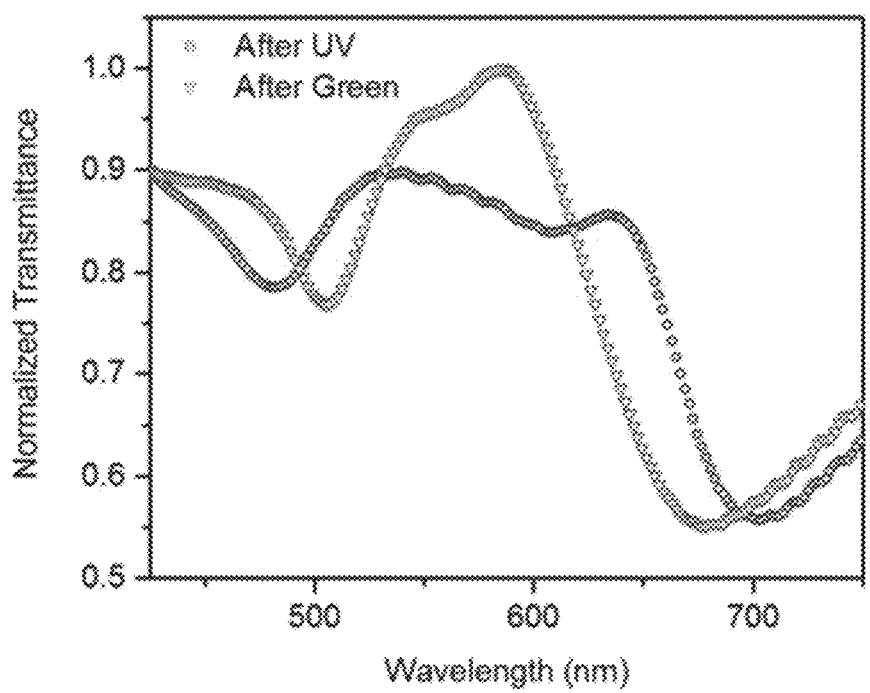
FIG. 42 is the transmission spectra showing reversible photoswitching of Rabi splitting in the hybrid plasmon-waveguide modes of the sample with $a_y$=370 nm. The single hybrid plasmon-waveguide mode after green light irradiation has a peak wavelength of 510 nm.
Figure 43:
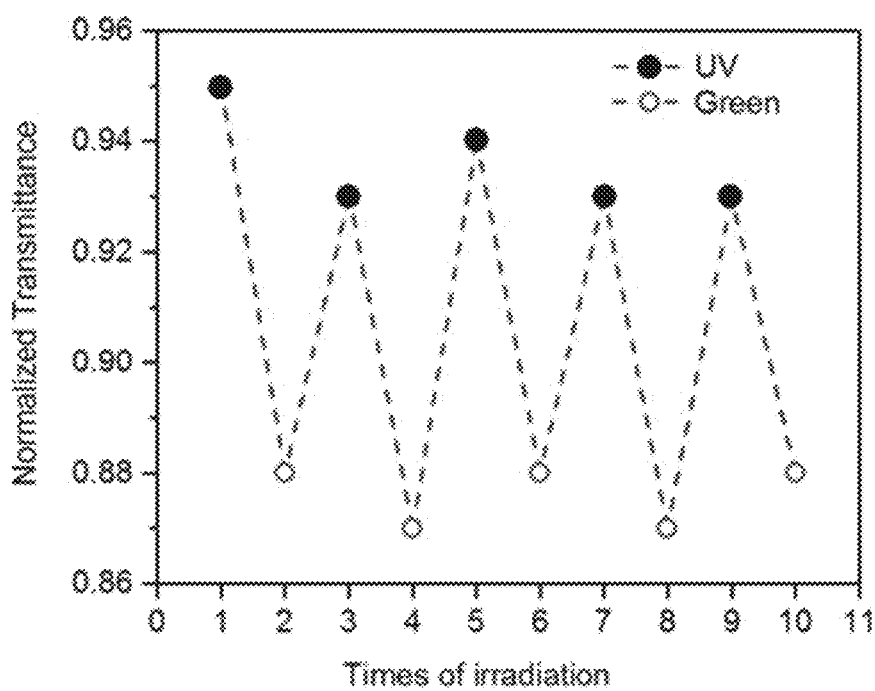
FIG. 43 shows the reversible modulation of the transmission intensity upon alternative UV and green light irradiation of the sample with $a_y$=370 nm. Each irradiation time was 2 minutes. The intensity was tracked at a wavelength of the diode-pumped solid state laser (i.e., 532 nm).

To further characterize the light propagation in the optically written waveguides, an Al nanodisk array with $a_y$=370 nm that was covered by the molecule-doped PMMA thin film was chosen. This hybrid system supports hybrid plasmon-waveguide mode with the peak wavelength close to the diode-pumped solid state laser (532 nm) when the molecules are at spiropyran state, as shown in FIG. 42 (see spectrum "After green"). The hybrid plasmon-waveguide mode can be repeatedly switched on and off by alternative irradiation to the sample with UV and green light due to the photoswitchable Rabi splitting (FIG. 43). The photoswitchability of spiropyran molecules can be compromised due to the fatigue of the photochromism after many cycles.

Figure 44:
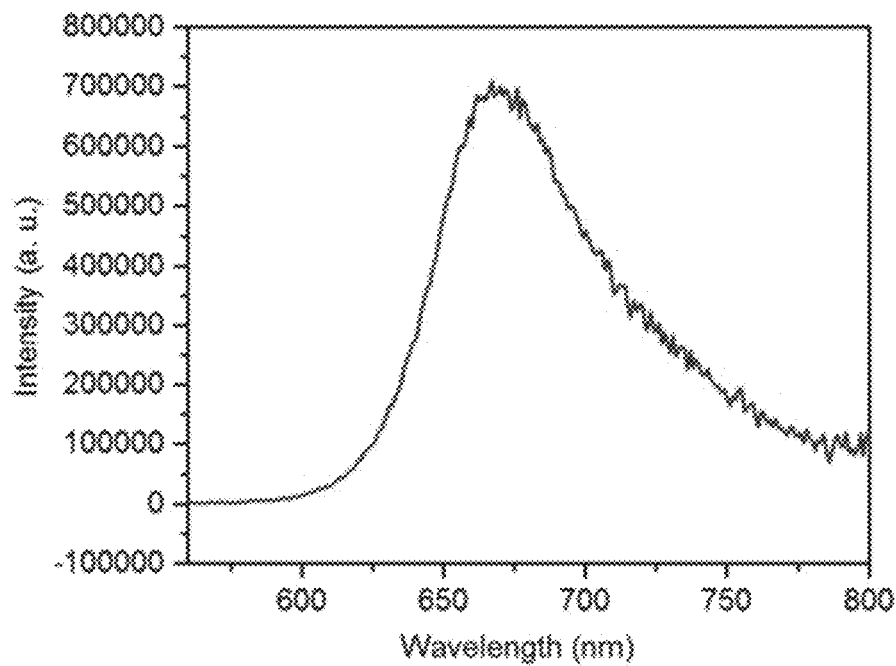
FIG. 44 is the fluorescence spectrum of merocyanine molecules at the excitation wavelength of 532 nm.
Figure 45:
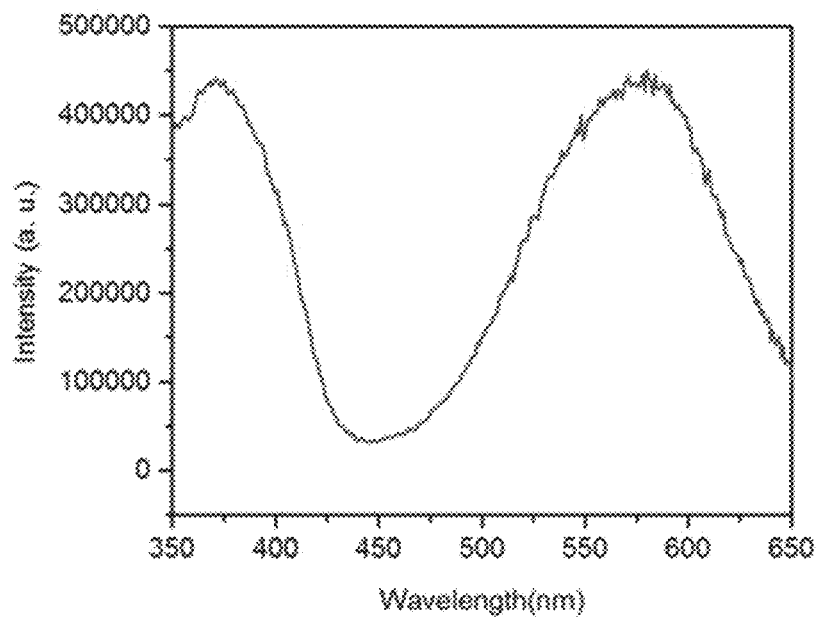
FIG. 45 is the excitation spectrum of merocyanine molecules at the emission wavelength of 667 nm.

FIG. 44 shows the fluorescence spectrum of merocyanine molecules, indicating the merocyanine molecules emit red light with a peak wavelength of 667 nm. The excitation spectrum of the merocyanine molecules recorded at the emission wavelength of 667 nm is displayed in FIG. 45, which confirms the feasibility of exciting fluorescence of merocyanine molecules with a 532 nm light.

Figure 46:
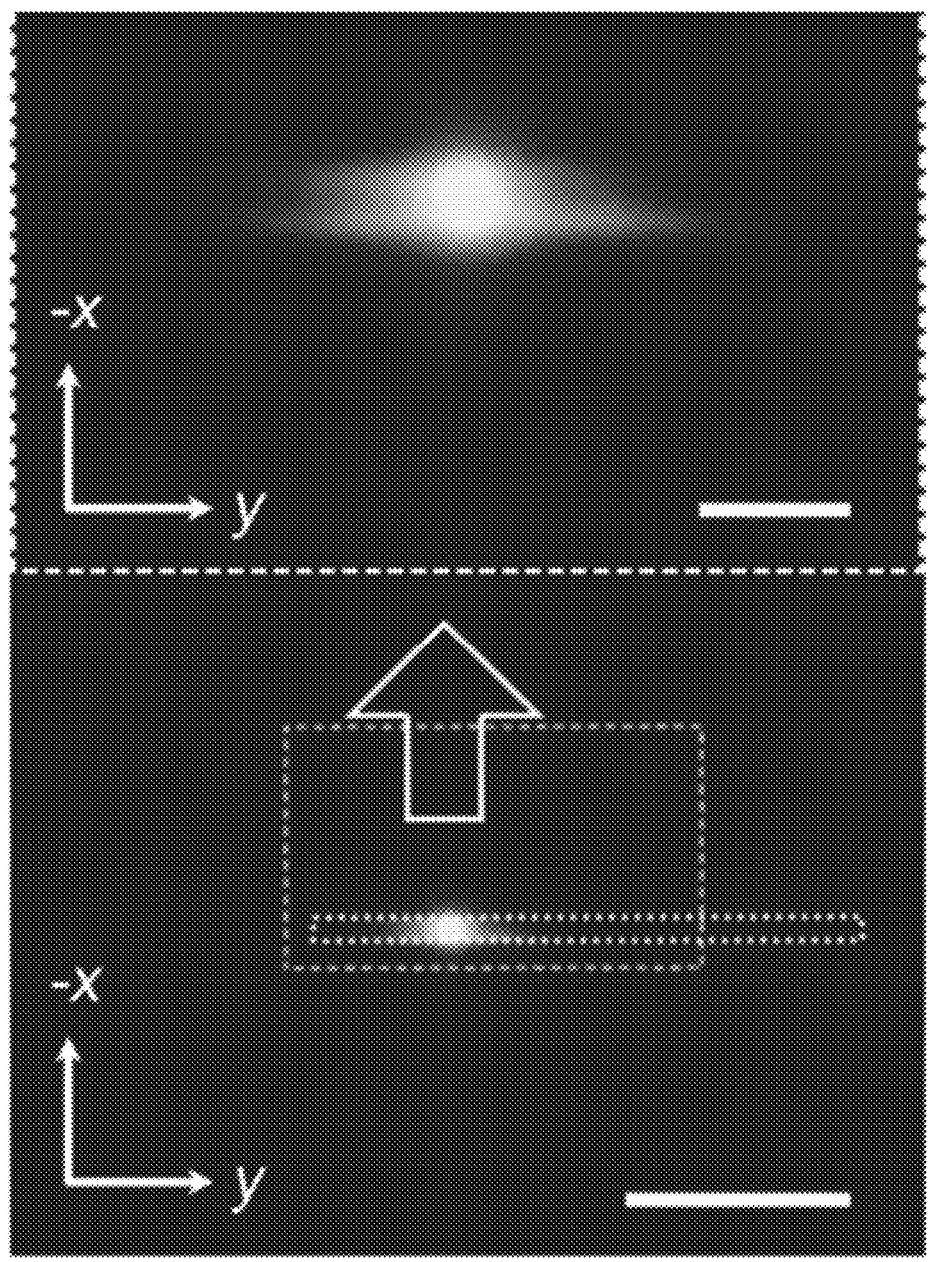
FIG. 46 is an optical image showing that a 532 nm laser beam is observed to couple to and propagate in an optically written waveguide on the molecule-doped PMMA on the Al nanodisk array. The yellow light propagates along the written waveguide outlined by the narrow dashed rectangle in the optical image at the bottom. The larger dashed rectangle indicates the Al nanodisk array. The top panel shows an enlarged image of the light spot shown in the bottom panel. Scale bars: 5 µm for the top panel and 20 µm for the bottom panel.

A linear waveguide was written on the hybrid structure (i.e., merocyanine molecule-doped PMMA+Al nanodisk array with $a_y$=370 nm) by scanning green laser beam along the y-axis of the sample. When a focused 532 nm laser beam (diameter=2 μm) was normally incident onto the waveguide, the light was observed to extend to both the left and right sides along the waveguide (FIG. 46); the yellow color of light to the mixture of red fluorescence of merocyanine molecules (Wang M et al. *J. Phys. Chem. C* 2016, 120, 14820-14827) and green light coupled to the waveguide.

Figure 47:
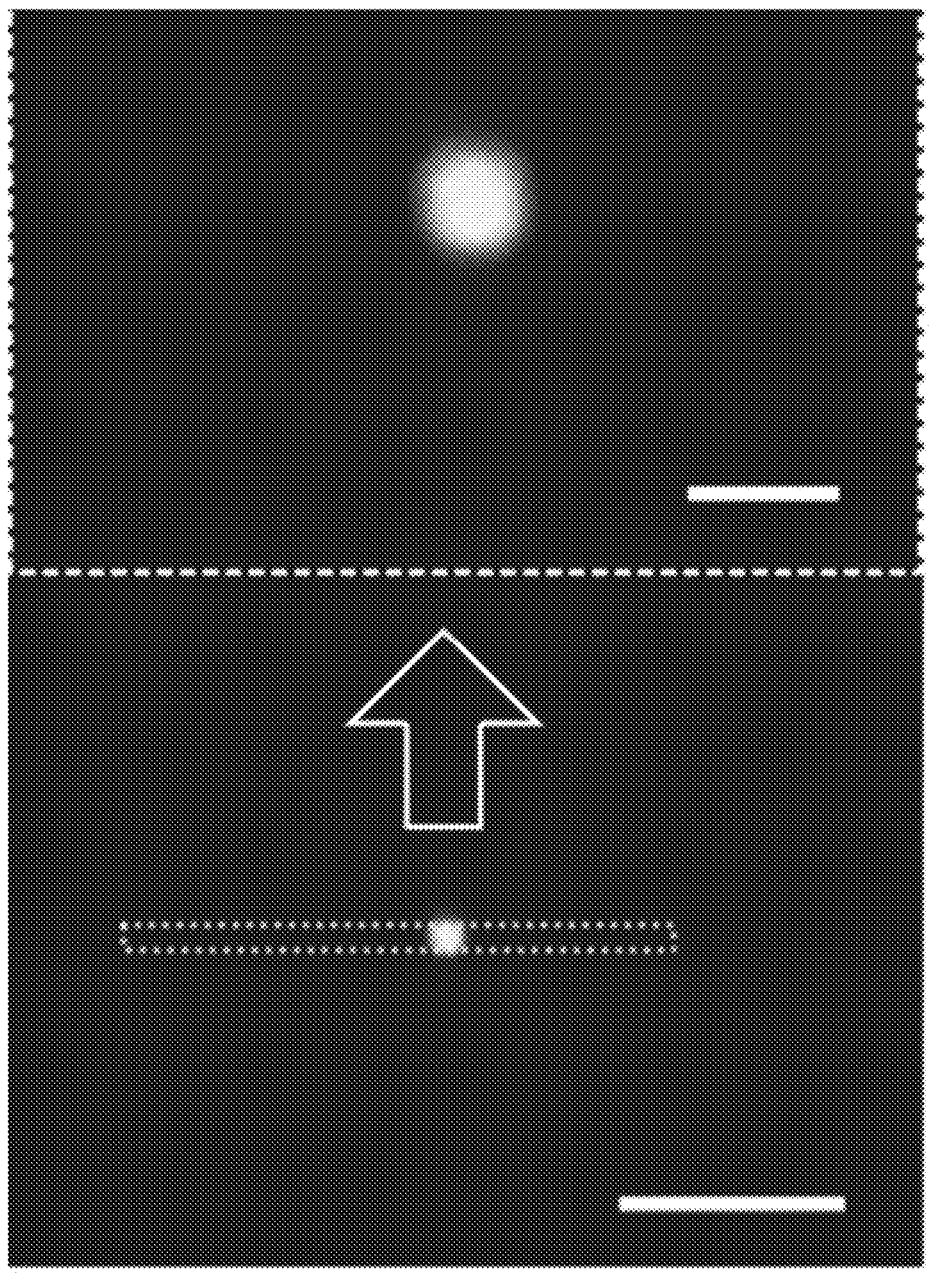
FIG. 47 is an optical image showing that no light coupling and propagation is observed when the 532 nm laser beam irradiated an optically written waveguide (outlined by the narrow dashed rectangle in the optical image at the bottom) on the molecule-doped PMMA without Al nanodisk array, which does not support the hybrid plasmon-waveguide modes. The top panel shows an enlarged image of the light spot shown in the bottom panel. Scale bars: 5 µm for the top panel and 20 µm for the bottom panel.
Figure 48:
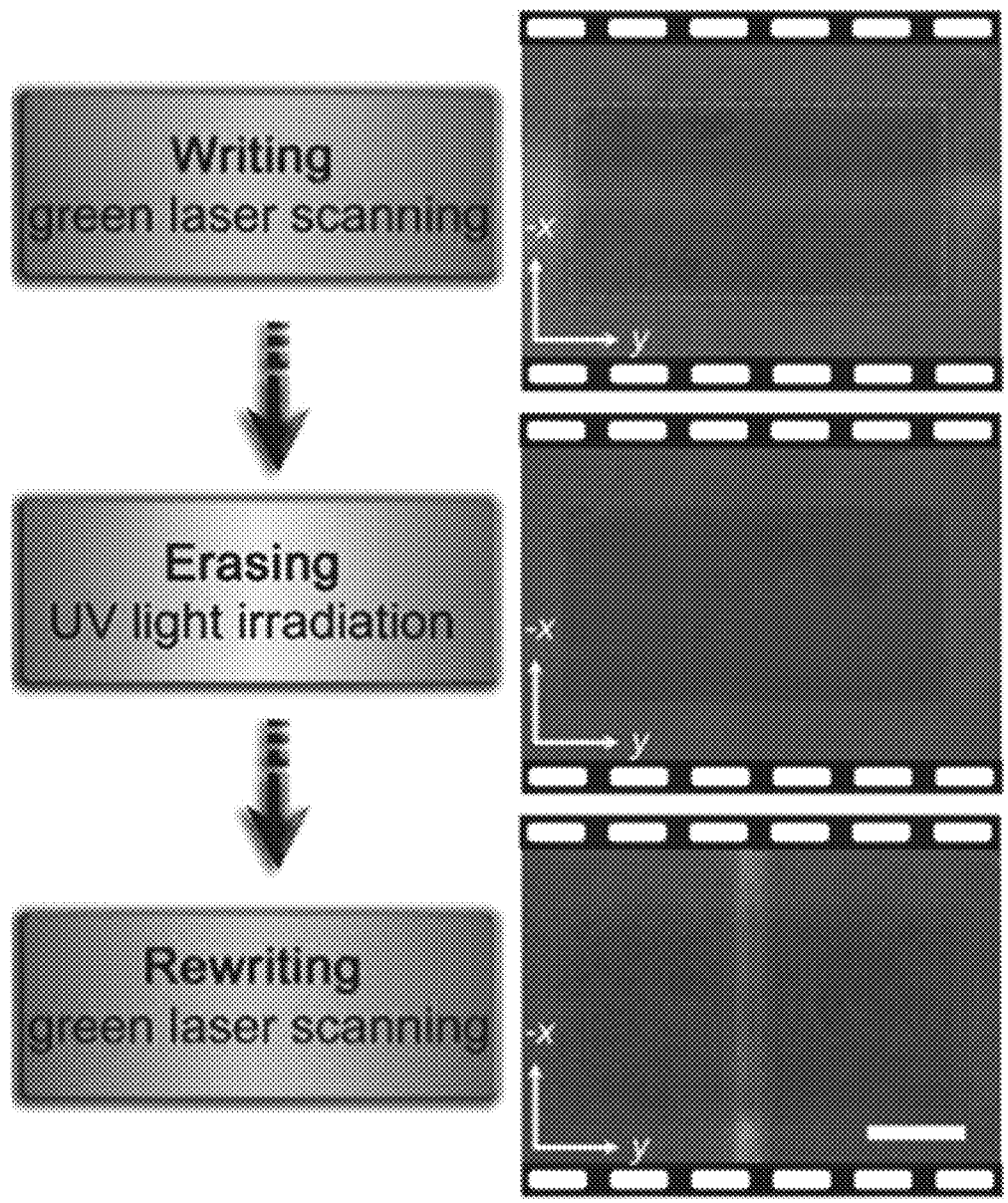
FIG. 48 is time-resolved optical images of the optically rewritable waveguides. The dark rectangular region outlined by the purple dashed rectangle is the Al nanodisk array. A waveguide (shown as a straight line) on the merocyanine-molecule-doped PMMA on Al nanodisk array is written with a focused green laser beam controlled by the digital micromirror device and a motorized stage. With green laser irradiation, the photochromic molecules were switched from merocyanine to spiropyran form. The waveguide was erased by UV light irradiation, and rewritten by green laser again. Scale bar: 10 µm.

The fluorescence and scattering light in the waveguide (mainly at the boundaries) allowed the light coupling and propagation in the far field to be visualized. In contrast, the same line pattern optically written on the merocyanine molecule-doped PMMA without an Al nanodisk array did not exhibit similar light coupling and propagation behavior, as shown in FIG. 47. Furthermore, the waveguides are optically rewritable in the hybrid plasmon-waveguide mode samples. As shown in FIG. 48, the waveguides can be erased and rewritten by alternative UV light irradiation and green laser scanning (Klajn R. *Chem. Soc. Rev.* 2014, 43, 148-184).

Hybrid plasmon-waveguide modes based on hybrid systems of Al nanodisk arrays covered by PMMA thin films doped with photochromic molecules were discussed herein, and photoswitchable Rabi splitting with a maximum splitting energy of 572 meV was demonstrated in the hybrid plasmon-waveguide modes by controlling the photoisomerization of the photochromic molecules. The Rabi splitting arises from the strong coupling between the hybrid plasmon-waveguide modes and molecular excitons. Reversible photoisomerization of the molecules leads to the photoswitchable strong coupling and Rabi splitting. The photoswitchable Rabi splitting enables the development of all-optical light modulators and optically rewritable waveguides. With the advantages of hybrid plasmon-waveguide modes in the long-range propagation of light with the subwavelength confinement, the reconfigurable optical elements based on the photoswitchable Rabi splitting will open up a new window of opportunities for compact photonic devices and lab-on-a-chip systems.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

What is claimed is:

1. A nanostructured photonic material, comprising:
   a substrate having a first surface;
   an array comprising a plurality of spaced-apart plasmonic particles disposed on the first surface of the substrate; and
   a waveguide layer disposed on the array and the first surface, wherein the waveguide layer:
      is optically coupled to the array,
      comprises a photochrome dispersed within a matrix material, and
      has an average thickness defining a hybrid plasmon waveguide mode;
   wherein the photochrome exhibits a first optical state and a second optical state; and
   wherein the second optical state of the photochrome at least partially overlaps with the hybrid plasmon waveguide mode.

2. The nanostructured photonic material of claim 1, wherein the substrate comprises glass, quartz, silicon dioxide, silicon nitride, a polymer, or a combination thereof.

3. The nanostructured photonic material of claim 1, wherein the plurality of plasmonic particles are each spaced apart from their nearest neighbors by a distance effective to define an array plasmon energy.

4. The nanostructured photonic material of claim 3, wherein the array plasmon energy does not substantially overlap with the hybrid plasmon waveguide mode.

5. The nanostructured photonic material of claim 1, wherein each of the plurality of plasmonic particles has an average characteristic dimension of from 20 nm to 1000 nm; an average thickness of from 10 nm to 200 nm; or a combination thereof.

6. The nanostructured photonic material of claim 1, wherein each of the plurality of plasmonic particles is disk-like in shape, such that the diameter of each disk is the average characteristic dimension of each of the plasmonic particles.

7. The nanostructured photonic material of claim 1, wherein the plurality of plasmonic particles comprise a plurality of metal particles.

8. The nanostructured photonic material of claim 7, wherein the plurality of metal particles comprise a metal selected form the group consisting of Au, Ag, Pt, Pd, Cu, Cr, Al, and combinations thereof.

9. The nanostructured photonic material of claim 1, wherein the array is defined by a unit cell, the unit cell having:
   a first principle axis and a second principle axis with an included angle between the first principle axis and the second principle axis;
      wherein the first principle axis has a length that is the distance separating each plasmonic particle in the array from its neighboring plasmonic particle (edge to edge) along the first principle axis;
      wherein the length of the first principle axis is two times the characteristic dimension of the plasmonic particles or less;
      wherein the second principle axis has a length that is the distance separating each plasmonic particle in the array from its neighboring plasmonic particle (edge to edge) along the second principle axis.

10. The nanostructured photonic material of claim 9, wherein the length of the first principle axis is from 5 nm to 1000 nm; the length of the second principle axis is from 50 nm to 2000 nm; the included angle is from 45° to 135°, or a combination thereof.

11. The nanostructured photonic material of claim 9, wherein the unit cell is in the shape of a triangle or a rectangle.

12. The nanostructured photonic material of claim 1, wherein the waveguide layer has an average thickness of from 100 nm to 300 nm.

13. The nanostructured photonic material of claim 1, wherein the matrix material comprises a polymer.

14. The nanostructured photonic material of claim 1, wherein the first optical state of the photochrome does not substantially overlap with the hybrid plasmon waveguide mode.

15. The nanostructured photonic material of claim 1, wherein the photochrome comprises spiropyran.

16. A system comprising:
   a nanostructured photonic material comprising:
      a substrate having a first surface;
      an array comprising a plurality of spaced-apart plasmonic particles disposed on the first surface of the substrate;
      a waveguide layer disposed on the array and the first surface, wherein the waveguide layer:
         is optically coupled to the array,
         comprises a photochrome dispersed within a matrix material, and
         has an average thickness defining a hybrid plasmon waveguide mode;
      wherein the photochrome exhibits a first optical state and a second optical state; and wherein the second optical state of the photochrome at least partially overlaps with the hybrid plasmon waveguide mode; and a first light source configured to illuminate the nanostructured photonic material.

* * * * *